(12) United States Patent
Dellinger et al.

(10) Patent No.: US 7,585,970 B2
(45) Date of Patent: *Sep. 8, 2009

(54) METHOD OF POLYNUCLEOTIDE SYNTHESIS USING MODIFIED SUPPORT

(75) Inventors: Douglas J Dellinger, Boulder, CO (US); Geraldine F Dellinger, Boulder, CO (US); John S Hargreaves, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 460 days.

This patent is subject to a terminal disclaimer.

(21) Appl. No.: 10/652,049

(22) Filed: Aug. 30, 2003

(65) Prior Publication Data
US 2005/0048496 A1 Mar. 3, 2005

(51) Int. Cl.
*C07H 21/00* (2006.01)

(52) U.S. Cl. ............... 536/25.34; 536/25.31; 536/25.33

(58) Field of Classification Search ............... 536/25.3, 536/25.31, 25.33, 26.7, 26.8, 27.6, 27.81, 536/28.5, 25.34, 28.53
See application file for complete search history.

(56) References Cited

U.S. PATENT DOCUMENTS

| | | | | |
|---|---|---|---|---|
| 4,500,707 A | * | 2/1985 | Caruthers et al. | 536/25.34 |
| 4,668,777 A | * | 5/1987 | Caruthers et al. | 536/26.5 |
| 6,222,030 B1 | * | 4/2001 | Dellinger et al. | 536/25.3 |
| 6,258,454 B1 | * | 7/2001 | Lefkowitz et al. | 428/333 |
| 6,630,581 B2 | * | 10/2003 | Dellinger et al. | 536/22.1 |
| 7,193,077 B2 | * | 3/2007 | Dellinger et al. | 536/25.3 |
| 2002/0045221 A1 | | 4/2002 | Dellinger et al. | |
| 2002/0058802 A1 | * | 5/2002 | Dellinger et al. | 536/25.31 |
| 2003/0129589 A1 | | 7/2003 | Koster et al. | |

FOREIGN PATENT DOCUMENTS

EP  1428810 A2  5/1999

OTHER PUBLICATIONS

Will et al., "The Synthesis Of Polyamide Nuceic Acids Using A Novel Monomethoxytrity Protecting-Group Strategy", Tetrahedron, vol. 51, No. 44, 1995, pp. 1269-1272.
Katzhendler et al,. "The Effect Of Spacer, Linkage And Solid Support On the Synthesis Of Oligonucleotides", Tetrahedron, vol. 45, No. 9, 1998, pp. 2777-2792.
European Search Report Dated: Oct. 28, 2004.

\* cited by examiner

*Primary Examiner*—Lawrence E. Crane

(57) ABSTRACT

A method for synthesizing a polynucleotide is disclosed. The method comprises providing a functionalized support comprising a triaryl methyl linker bound to the solid support through a substitution on one of the aryl groups, a nucleotide chain bound to the central methyl carbon of the triaryl methyl group and a nucleoside with a reactive site hydroxyl. The method further provides contacting that functionalized support with a precursor having a hydroxyl protecting group and a phosphorous derivative reactive group to produce internucleotide linkage. The resulting compound is then treated to both remove the hydroxyl protecting group on the precursor, and to oxidize the internucleotide bond.

20 Claims, 3 Drawing Sheets

METHOD OF POLYNUCLEOTIDE SYNTHESIS USING MODIFIED SUPPORT

This invention was made with Government support under Agreement No. N39998-01-9-7068. The Government has certain rights in the invention.

RELATED APPLICATIONS

Related subject matter is disclosed in U.S. Patent Applications entitled "Method for Polynucleotide Synthesis", (Ser. No. 10/652,054); "Cleavable Linker for Polynucleotide Synthesis", (Ser. No. 10/652,063); "Exocyclic Amine Triaryl Methyl Protecting Groups in Two-Step Polynucleotide Synthesis" (Ser. No. 10/652,064); "Precursors For Two-Step Polynucleotide Synthesis" (Ser. No. 10/652,048); all applications filed in the names of Dellinger et al. on Aug. 30, 2003, the same day as the instant application, all of which are incorporated herein by reference in their entireties, provided that, if a conflict in definition of terms arises, the definitions provided in the present application shall be controlling.

1. Field of the Invention

The invention relates generally to nucleic acid chemistry and to the chemical synthesis of polynucleotides. More particularly, the invention relates to modifying a support for use in polynucleotide synthesis to provide for release of the synthesized polynucleotides from the support. The invention is useful in the manufacture of reagents and devices used in the fields of biochemistry, molecular biology and pharmacology, and in medical diagnostic and screening technologies.

2. Background of the Invention

Solid phase chemical synthesis of DNA fragments is routinely performed using protected nucleoside phosphoramidites. Beaucage et al. (1981) Tetrahedron Lett. 22:1859. In this approach, the 3'-hydroxyl group of an initial 5'-protected nucleoside is first covalently attached to the polymer support. Pless et al. (1975) Nucleic Acids Res. 2:773. Synthesis of the oligonucleotide then proceeds by deprotection of the 5'-hydroxyl group of the attached nucleoside, followed by coupling of an incoming nucleoside-3'-phosphoramidite to the deprotected hydroxyl group. Matteucci et al. (1981) J. Am. Chem. Soc. 103:3185. The resulting phosphite triester is finally oxidized to a phosphorotriester to complete one round of the synthesis cycle. Letsinger et al. (1976) J. Am. Chem. Soc. 98:3655. The steps of deprotection, coupling and oxidation are repeated until an oligonucleotide of the desired length and sequence is obtained. This process is illustrated schematically in FIG. 1 (wherein "B" represents a purine or pyrimidine base, "DMT" represents dimethoxytrityl and "iPR" represents isopropyl). Optionally, after the coupling step, the product may be treated with a capping agent designed to esterify failure sequences and cleave phosphite reaction products on the heterocyclic bases.

The chemical group conventionally used for the protection of nucleoside 5'-hydroxyls is dimethoxytrityl, which is removable with acid. Khorana (1968) Pure Appl. Chem. 17:349; Smith et al. (1962) J. Am. Chem. Soc. 84:430. This acid-labile protecting group provides a number of advantages for working with both nucleosides and oligonucleotides. For example, the DMT group can be introduced onto a nucleoside regioselectively and in high yield. Brown et al. (1979) Methods in Enzymol. 68:109. Also, the lipophilicity of the DMT group greatly increases the solubility of nucleosides in organic solvents, and the carbocation resulting from acidic deprotection gives a strong chromophore, which can be used to indirectly monitor coupling efficiency. Matteucci et al. (1980) Tetrahedron Lett. 21:719. In addition, the hydrophobicity of the group can be used to aid separation on reverse-phase HPLC. Becker et al. (1985) J. Chromatogr. 326:219.

However, the use of DMT as a hydroxyl-protecting group for conventional oligonucleotide synthesis has a number of perceived drawbacks. The N-glycosidic linkages of oligodeoxyribonucleotides are susceptible to acid catalyzed cleavage (Kochetkov et al., Organic Chemistry of Nucleic Acids (New York: Plenum Press, 1972)), and even when the protocol is optimized, recurrent removal of the DMT group with acid during oligonucleotide synthesis results in depurination. Shaller et al. (1963) J. Am. Chem. Soc. 85:3821. The N-6-benzoyl-protected deoxyadenosine nucleotide is especially susceptible to glycosidic cleavage, resulting in a substantially reduced yield of the final oligonucleotide. Efcavitch et al. (1985) Nucleosides & Nucleotides 4:267. Attempts have been made to address the problem of acid-catalyzed depurination utilizing alternative mixtures of acids and various solvents; see, for example, Sonveaux (1986) Bioorganic Chem. 14:274. However, this approach has met with limited success. McBride et al. (1986) J. Am. Chem. Soc. 108:2040. Also, using the conventional synthesis scheme set forth in FIG. 1 requires additional steps per cycle of addition of a nucleotide to the growing polynucleotide chain, including the post-coupling deprotection step in which the DMT group is removed following oxidation of the internucleotide phosphite triester linkage to a phosphorotriester.

The problems associated with the use of DMT are exacerbated in solid phase oligonucleotide synthesis where "microscale" parallel reactions are taking place on a very dense, packed surface. Applications in the field of genomics and high throughput screening have fueled the demand for precise chemistry in such a context. Side-reactions, which are known to occur at detectable but acceptable levels during routine synthesis, can rise to unacceptable levels under the conditions required for these expanded applications. Thus, increasingly stringent demands are placed on the chemical synthesis cycle as it was originally conceived, and the problems associated with conventional methods for synthesizing oligonucleotides are rising to unacceptable levels in these expanded applications.

Recently, alternate schemes for synthesis of polynucleotides have been described. See, e.g. U.S. Pat. No. 6,222,030 to Dellinger et al., U.S. Pat. Appl'n Publ'n No. US2002/0058802 A1 to Dellinger et al., Seio et al. (2001) Tetrahedron Lett. 42 (49):8657-8660. These schemes involve protecting groups other than DMT at the 3' or 5' positions and correspondingly different conditions for performing reactions such as deprotection at the 3' or 5' positions. These schemes have the additional advantage of reducing the number of steps required per cycle of addition of a nucleotide to the growing polynucleotide chain. FIG. 2 illustrates such a process having a two-step synthesis cycle, represented in FIG. 2 as a coupling step and a simultaneous deprotection and oxidation step.

In previously reported methods such as that shown in FIG. 1, the newly synthesized oligonucleotides containing N-protected nucleobases are typically deprotected using displacement by nucleophiles such as ammonia or methylamine. These reagents can have similar properties to (and thus may not be compatible with) the reagents used for the alternative removal of 3' or 5' protecting groups in simplified 2-step DNA synthesis.

Solid phase polynucleotide synthesis results in a polynucleotide bound upon a solid support. Typically, an additional step releases the polynucleotide from the solid support after the polynucleotide strand has been synthesized. This release step yields the polynucleotide in solution, which may then be separated from the solid support, e.g. by filtration or other suitable methods. The release step is dependent upon having a support that is functionalized with a releasable moiety that, while inert under the conditions used in the synthesis cycle, provides for the release of the synthesized polynucleotide under conditions conducive for doing so.

What is needed is an improved method for the synthesis of polynucleotides providing for the release of the synthesized polynucleotide from the support.

SUMMARY OF THE INVENTION

The invention addresses the aforementioned deficiencies in the art, and provides novel methods for synthesis of polynucleotides. More specifically, the invention provides a method of synthesizing a polynucleotide upon a support having a releasable linker group. Such methods involve forming an internucleotide bond by contacting a functionalized support having the structure (Id)

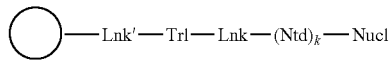
(Id)

with a precursor having the structure (IId)

Rag-Sugar-Base (IId)

under conditions and for a time sufficient to result in internucleotide bond formation.

In an embodiment, the method of synthesizing polynucleotides further includes, after the internucleotide bond is formed, exposing the result of the forming an internucleotide bond step to a composition which concurrently oxidizes the internucleotide bond and removes a hydroxylprotecting group from the Sugar group.

The functionalized support employed in the current invention typically has the structure (Id)

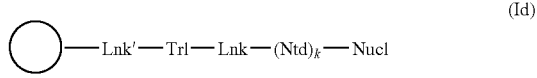
(Id)

Wherein the groups are defined as follows:

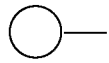

is a solid support,

Trl- is a triaryl methyl linker group having one or more substituents on the aryl groups, Lnk'- is a linking group linking the solid support and the triaryl methyl linker group, or is a bond linking the solid support and the triaryl methyl linker group, $(Ntd)_k$- is a polynucleotide moiety having k nucleotide sub-units, wherein k is an integer in the range from zero to about 200, Lnk- is a linking group linking the triaryl methyl linker group and the polynucleotide moiety, or is a bond linking the triaryl methyl linker group and polynucleotide moiety, and Nucl- is a nucleoside moiety having a reactive site hydroxyl.

The precursors used in the current invention typically have the structure (IId):

Rag-Sugar-Base (IId)

Wherein the groups are defined as follows:

Rag—a reactive group capable of reacting with a reactive site hydroxyl of a nucleoside moiety (e.g. on a nascent polynucleotide molecule in the process of being synthesized) to result in formation of an internucleotide bond, Sugar—a sugar group such as may be found in a nucleotide or nucleotide analog, typically ribose or 2'-deoxyribose, wherein the sugar group is substituted with one or more substituents, and Base—a heterocyclic base, typically attached to the sugar group at the 1' position of the sugar group.

The present invention provides methods of synthesizing polynucleotides using functionalized supports and precursors described herein. Such methods involve forming an internucleotide bond by contacting a functionalized support with a precursor under conditions and for a time sufficient to result in internucleotide bond formation. In the method, the functionalized support comprises a nucleoside moiety having a reactive site hydroxyl, wherein the nucleoside moiety is attached to a solid support via a triaryl methyl linker group.

In an embodiment, the method of synthesizing polynucleotides further includes, after the internucleotide bond is formed, exposing the result of the forming an internucleotide bond step to a composition which concurrently oxidizes the internucleotide bond and removes a hydroxylprotecting group from the sugar group.

Further information about the groups described above, functionalized supports having the structure (Id), precursors having the structure (IId), and use of such functionalized supports and precursors in synthesis of polynucleotides is described herein. The use of a triaryl methyl linker group allows the synthesized polynucleotide to be released from the solid support under acidic conditions.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the materials and methods particularly pointed out in the appended claims.

BRIEF DESCRIPTION OF THE DRAWINGS

These and other features of the invention will be understood from the description of representative embodiments of the method herein and the disclosure of illustrative materials for carrying out the method, taken together with the Figures, wherein FIG. 1 schematically illustrates prior art synthesis of polynucleotides.

To facilitate understanding, identical reference numerals have been used, where practical, to designate corresponding elements that are common to the Figures. Figure components are not drawn to scale.

DETAILED DESCRIPTION

Figure 1:
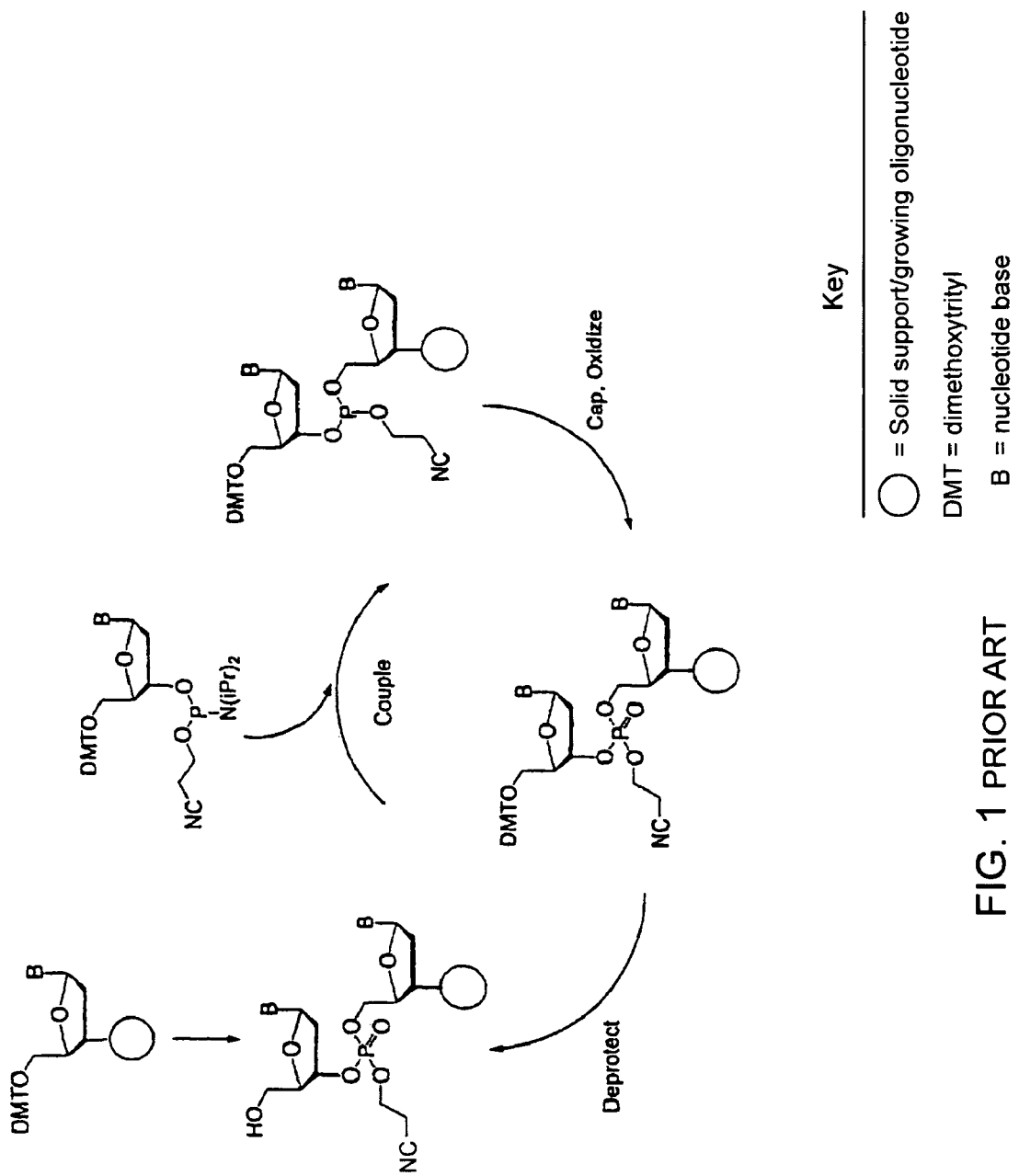

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an insoluble support" includes a plurality of insoluble supports. In this specification and in the claims that follow, reference will be made to a number of terms that shall be defined to have the following meanings unless a contrary intention is apparent:

A "nucleotide" refers to a sub-unit of a nucleic acid (whether DNA or RNA or analogue thereof) which includes a phosphate group, a sugar group and a heterocyclic base, as well as analogs of such sub-units. A "nucleoside" references a nucleic acid subunit including a sugar group and a heterocyclic base. A "nucleoside moiety" refers to a portion of a molecule having a sugar group and a heterocyclic base (as in a nucleoside); the molecule of which the nucleoside moiety is a portion may be, e.g. a polynucleotide, oligonucleotide, or nucleoside phosphoramidite. A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer. A "polynucleotide intermediate" references a molecule occurring between steps in chemical synthesis of a polynucleotide, where the polynucleotide intermediate is subjected to further reactions to get the intended final product, e.g. a phosphite intermediate which is oxidized to a phosphate in a later step in the synthesis, or a protected polynucleotide which is then deprotected. An "oligonucleotide" generally refers to a nucleotide multimer of about 2 to 200 nucleotides in length, while a "polynucleotide" includes a nucleotide multimer having at least two nucleotides and up to several thousand (e.g. 5000, or 10,000) nucleotides in length. It will be appreciated that, as used herein, the terms "nucleoside", "nucleoside moiety" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N-6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "modified alkyl" refers to an alkyl group having from one to twenty-four carbon atoms, and further having additional groups, such as one or more linkages selected from ether-, thio-, amino-, phosphor oxo-, ester-, and amido-, and/or being substituted with one or more additional groups including lower alkyl, aryl, alkoxy, thioalkyl, hydroxyl, amino, sulfonyl, thio, mercapto, imino, halo, cyano, nitro, nitroso, azido, carboxy, sulfide, sulfone, sulfoxy, phosphoryl, silyl, silyloxy, and boronyl. The term "modified lower alkyl" refers to a group having from one to six carbon atoms and further having additional groups, such as one or more linkages selected from ether-, thio-, amino-, phosphor keto-, ester- and amido-, and/or being substituted with one or more groups including lower alkyl; aryl, alkoxy, thioalkyl, hydroxyl, amino, sulfonyl, thio, mercapto, imino, halo, cyano, nitro, nitroso, azido, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of $C_5$ and $C_6$) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to six carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to six carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more substituents typically selected from the group consisting of lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl thio, mercapto, amino, imino, halo, cyano, nitro, nitroso, azido, carboxy, sulfide, sulfone, sulfoxy, phosphoryl, silyl, silyloxy, and boronyl. Typical aryl groups contain 1 to 3 fused aromatic rings, and more typical aryl groups contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH$_2$)$_j$—Ar wherein j is an integer in the range of 1 to 24, more typically 1 to 6, and Ar is a monocyclic aryl moiety.

The term "electron withdrawing" denotes the tendency of a substituent to attract valence electrons of the molecule of which it is a part, i.e., an electron-withdrawing substituent is electronegative.

The term "alpha effect," as in an "alpha effect" nucleophilic deprotection reagent, is used to refer to an enhancement of nucleophilicity that is found when the atom adjacent a nucleophilic site bears a lone pair of electrons. As the term is used herein, a nucleophile is said to exhibit an "alpha effect" if it displays a positive deviation from a Bronsted-type nucleophilicity plot. Hoz et al. (1985) Israel J. Chem. 26:313. See also, Aubort et al. (1970) Chem. Comm. 1378; Brown et al. (1979) J. Chem. Soc. Chem. Comm.171; Buncel et al. (1982) J. Am. Chem. Soc. 104:4896; Edwards et al. (1962) J. Am. Chem. Soc. 84:16; Evanseck et al. (1987) J. Am. Chem Soc. 109:2349. The magnitude of the alpha effect is dependent upon the electrophile which is paired with the specific nucleophile. McIsaac, Jr. et al. (1972), J. Org. Chem. 37:1037. Peroxy anions are example of nucleophiles which exhibit strong alpha effects.

The term "heterocyclic" refers to a five- or six-membered monocyclic structure or to an eight- to eleven-membered bicyclic structure which is either saturated or unsaturated. The heterocyclic groups herein may be aliphatic or aromatic. Each heterocyclic group consists of carbon atoms and from one to four heteroatoms selected from the group consisting of nitrogen, oxygen and sulfur. As used herein, the term "nitrogen heteroatoms" includes any oxidized form of nitrogen and the quaternized form of nitrogen. The term "sulfur heteroatoms" includes any oxidized form of sulfur. Examples of heterocyclic groups include purine, pyrimidine, piperidinyl, morpholinyl and pyrrolidinyl. "Heterocyclic base" refers to any natural or non-natural heterocyclic moiety that can participate in base pairing or base stacking interaction on an oligonucleotide strand.

"Exocyclic" refers to a group situated outside of the ring of a cyclic chemical structure, e.g. a portion of a substituent of the ring is exocyclic to the ring. As used herein, exocyclic amine refers to an amine group that is a substituent of a ring of a heterocyclic base and includes embodiments in which the nitrogen of the amine group is attached directly to a member of the ring structure and also includes embodiments in which the nitrogen of the amine group may be linked to the ring structure of the heterocyclic base via an intervening group.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond may comprise a phospho or phosphite group, and may include linkages where one or more oxygen atoms of the phospho or phosphite group are either modified with a substituent or replaced with another atom, e.g. a sulfur atom or the nitrogen atom of a mono- or di-alkyl amino group.

"Moiety" and "group" are used to refer to a portion of a molecule, typically having a particular functional or structural feature, e.g. a linking group (a portion of a molecule connecting two other portions of the molecule), or an ethyl moiety (a portion of a molecule with a structure closely related to ethane). A "triaryl methyl linker group" as used herein references a triaryl methyl group having one or more substituents on the aromatic rings of the triaryl methyl group, wherein the triaryl methyl group is bonded to two other moieties such that the two other moieties are linked via the triaryl methyl group.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"Bound" may be used herein to indicate direct or indirect attachment. In the context of chemical structures, "bound" (or "bonded") may refer to the existence of a chemical bond directly joining two moieties or indirectly joining two moieties (e.g. via a linking group). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "halo" or "halogen" is used in its conventional sense to refer to a chloro, bromo, fluoro or iodo substituent.

By "protecting group" as used herein is meant a species which prevents a portion of a molecule from undergoing a specific chemical reaction, but which is removable from the molecule following completion of that reaction. This is in contrast to a "capping group," which permanently binds to a segment of a molecule to prevent any further chemical transformation of that segment. A "hydroxylprotecting group" refers to a protecting group where the protected group is a hydroxyl. "Reactive site hydroxyl" references a hydroxyl group capable of reacting with a precursor to result in an internucleotide bond being formed. In typical embodiments, the reactive site hydroxyl is the terminal 5'-hydroxyl during 3'-5' polynucleotide synthesis and is the 3'-hydroxyl during 5'-3' polynucleotide synthesis. An "acid labile protected hydroxyl" is a hydroxyl group protected by a protecting group that can be removed by acidic conditions. Similarly, an "acid stabile protected hydroxyl" is a hydroxyl group protected by a protecting group that is not removed (is stabile) under acidic conditions. An "acid labile linking group" is a linking group that releases a linked group under acidic conditions. A trityl group is a triphenyl methyl group, in which one or more of the phenyl groups of the triphenyl methyl group is optionally substituted. A "substituted trityl group" or a "substituted triphenyl methyl group" is a triphenyl methyl group on which one of the hydrogens of the phenyl groups of the triphenyl methyl group is replaced by a substituent.

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, boronyl, and modified lower alkyl.

A "group" includes both substituted and unsubstituted forms. Typical substituents include one or more lower alkyl, modified alkyl, any halogen, hydroxyl, or aryl. Any substituents are typically chosen so as not to substantially adversely affect reaction yield (for example, not lower it by more than 20% (or 10%, or 5% or 1%) of the yield otherwise obtained without a particular substituent or substituent combination).

Hyphens, or dashes, are used at various points throughout this specification to indicate attachment, e.g. where two named groups are immediately adjacent a dash in the text, this indicates the two named groups are attached to each other. Similarly, a series of named groups with dashes between each of the named groups in the text indicates the named groups are attached to each other in the order shown. Also, a single named group adjacent a dash in the text indicates the named group is typically attached to some other, unnamed group. In some embodiments, the attachment indicated by a dash may be, e.g. a covalent bond between the adjacent named groups. In some other embodiments, the dash may indicate indirect attachment, i.e. with intervening groups between the named groups. At various points throughout the specification a group may be set forth in the text with or without an adjacent dash, (e.g. amido or amido-, further e.g. Trl or Trl-, yet further e.g. Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g. the Sugar group, herein; further e.g. where a linkage is intended, such as linking groups).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

Accordingly, an embodiment in accordance with the invention is directed to a method for synthesizing polynucleotides using functionalized supports and precursors described herein. The embodiment comprises forming an internucleotide bond by contacting a precursor with a functionalized support under conditions and for a time sufficient to result in formation of the internucleotide bond. In the method, the functionalized support comprises a nucleoside moiety having a reactive site hydroxyl, a triaryl methyl linker group, and a solid support, the nucleoside moiety attached to the solid support via the triaryl methyl linker group.

In an embodiment, the method of synthesizing polynucleotides further includes, after the internucleotide bond is formed, exposing the result of the forming an internucleotide bond step to a composition which concurrently oxidizes the internucleotide bond and removes a hydroxylprotecting group.

The functionalized support employed in the method of the current invention typically has the structure (Id)

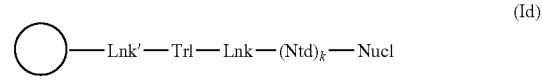
(Id)

Wherein the groups are defined as follows:

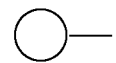

is a solid support,

Trl- is the triaryl methyl linker group, the triaryl methyl linker group having three aryl groups, each of the three aryl groups bound to a central methyl carbon, at least one of said three aryl groups having one or more substituents, Lnk'- is a linking group linking the solid support and the triaryl methyl linker group, or is a bond linking the solid support and the triaryl methyl linker group, $(Ntd)_k$- is a polynucleotide moiety having k nucleotide sub-units, wherein k is an integer in the range from zero to about 200, Lnk- is a linking group linking the triaryl methyl linker group and the polynucleotide moiety, or is a bond directly linking the triaryl methyl linker group and the polynucleotide moiety, and Nucl- is a nucleoside moiety having a reactive site hydroxyl.

The precursors employed in the method of the current invention typically have the structure (IId)

Rag-Sugar-Base (IId)

Wherein the groups are defined as follows:

Rag—a reactive group capable of reacting with a reactive site hydroxyl of a nucleoside moiety (e.g. on a nascent polynucleotide molecule in the process of being synthesized) to result in formation of an internucleotide bond; the reactive group is typically a phosphorus derivative as described below in reference to structure (IVd), Sugar—a sugar group such as may be found in a nucleotide or nucleotide analog, typically ribose, 2'-deoxyribose, arabinose, xylose, or lyxose wherein the sugar group is substituted with one or more substituents, and Base—a heterocyclic base, typically attached to the sugar group at the 1' position of the sugar group.

The sugar group may be any sugar group (or substituted sugar group) known in the art of nucleotide synthesis and nucleotide analog synthesis. The skilled practitioner will appreciate that polynucleotide analogs may be accomplished using such known sugars. Representative sugar groups may be selected from monosaccharides, ketoses, aldoses, pentoses (five carbon sugars), hexoses (six carbon sugars), including any such groups modified by e.g. oxidation, deoxygenation, introduction of other substituents, alkylation and acylation of hydroxyl groups, and chain branching. The sugar group is typically ribose or 2'-deoxyribose, although other sugars may be used. In an embodiment, the sugar is arabinose. In another embodiment, the sugar is selected from xylose or lyxose. In typical embodiments, the sugar group is a monosaccharide; representative monosaccharides include glycerose, dihydroxyacetone, erythrose, erythrulose, xylose, lyxose, arabinose, ribose, xylulose, ribulose, rhamnose, fucose, glucose, mannose, galactose, fructose, sorbose, glucoheptose, galamannoheptose, sedoheptulose, mannoheptulose, and others.

In certain embodiments, the sugar group is a polyhydroxyketone having the structure (IIIad)

H—[CH(OH)]$_n$—C(=O)—[CH(OH)]$_m$—H  (IIIad)

in which n is an integer from 1 to about 5 and m is an integer from 1 to about 5; provided that one of the hydrogens or hydroxyls in structure (IIIad) is replaced by the reactive group; and provided that the heterocyclic base is directly bound to one of the carbons of structure (IIIad) (thereby replacing a hydrogen or hydroxyl of structure (IIIad) or adding to the carbonyl carbon of structure (IIIad)). It will be readily apparent to the reader skilled in the art that, in embodiments in which the heterocyclic base is added to (i.e. bound directly to) the carbonyl carbon of structure (IIIad), the other groups (e.g. the carbonyl oxygen) bound to the carbonyl carbon may be changed to preserve normal valency rules for the groups, e.g. to hydroxyl, hydrido, or other suitable groups. Typically, the polyhydroxyketone has at least three carbon atoms, typically at least four carbon atoms, more typically at least five carbon atoms, and typically has up to about eight carbon atoms, more typically up to about ten carbon atoms. In particular embodiments, the sugar group is based on the given structure in this paragraph but is modified, e.g. by deoxygenation, by introduction of other substituents (e.g. replacement of a hydrogen or hydroxyl by a substituent), by alkylation and/or acylation of hydroxyl groups, by chain branching, and by formation of an intramolecular hemiacetal, and by combinations of the above. Also contemplated are sugar groups in which the given structure (IIIad) is modified by intramolecular cyclization reaction, e.g. forming a furanose, pyranose, or other ring structure. As used herein, a sugar group "based on" structure (IIIad) references any structure disclosed in this paragraph, also encompassing the modifications to structure (IIIad) as described in this paragraph.

In certain embodiments, the sugar group is a polyhydroxyaldehyde having the structure

H—[CH(OH)]$_n$—C(=O)H  (IIIbd)

in which n is an integer from 2 to about 8, typically from 3 to 7, more typically from 4 to 6; provided that one of the hydrogens or hydroxyls in structure (IIIbd) is replaced by the reactive group; and provided that the heterocyclic base is directly bound to one of the carbons of structure (IIIbd) (thereby replacing a hydrogen or hydroxyl of structure (IIIbd) or adding to the carbonyl carbon of structure (IIIbd)). It will be readily apparent to the reader skilled in the art that, in embodiments in which the heterocyclic base is added to (i.e. bound directly to) the carbonyl carbon of structure (IIIbd), the other groups (e.g. the carbonyl oxygen, the aldehydic hydrogen) bound to the carbonyl carbon may be changed to preserve normal valency rules for the groups, e.g. to hydroxyl, hydrido, or other suitable groups. In particular embodiments, the sugar group is based on the given structure in this paragraph but is modified, e.g. by deoxygenation, by introduction of other substituents (e.g. replacement of a hydrogen or hydroxyl by a substituent), by alkylation and/or acylation of hydroxyl groups, by chain branching, and by formation of an intramolecular hemiacetal, and by combinations of the above. Also contemplated are sugar groups in which the given structure (IIIbd) is modified by intramolecular cyclization reaction, e.g. forming a furanose, pyranose, or other ring structure. As used herein, a sugar group "based on" structure (IIIbd) references any structure disclosed in this paragraph, also encompassing the modifications to structure (IIIbd) as described in this paragraph.

The sugar group of the precursor is substituted with one or more substituents, e.g. the reactive group and the hydroxyl protecting group as described herein. In typical embodiments, the precursor has the structure (IVd)

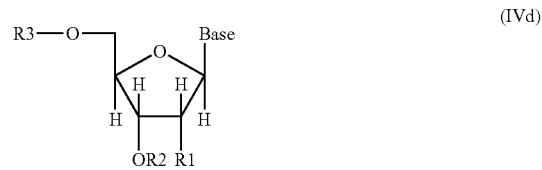

Wherein the groups are defined as follows:

O and H represent oxygen and hydrogen, respectively

R1 is typically hydrido or hydroxyl (or hydroxylprotecting group), wherein when R1 is hydrido, the sugar is 2'-deoxyribose, as will be present in DNA synthesis, and when R1 is hydroxyl (or hydroxylprotecting group), the sugar is ribose, as will be present in RNA synthesis. In certain embodiments, R1 is lower alkyl, modified lower alkyl, or alkoxy.

One of R2 or R3 is a hydroxyl protecting group releasable under conditions of simultaneous deprotection and oxidation during the polynucleotide synthesis cycle, as further described herein; and the other of R2 or R3 is a reactive group (Rag-) as referenced above with regard to structure (IId). Under appropriate conditions as described herein, the reactive group specifically reacts with a reactive site hydroxyl such that the desired product of the reaction is achieved in acceptable yield. In this regard, "specifically reacts" means that an acceptable amount of precursor reacts as described herein with the nucleoside moiety to result in internucleotide bond formation in acceptable yield. In various embodiments, the acceptable yield is at least about 5%, at least about 10%, at least about 20%, at least about 30%, at least about 50%, or even more, where the percent indicated is the proportion of precursor incorporated (in moles) over the theoretical amount of precursor (in moles) that would be incorporated if the reaction was 100% completed, expressed as a percent. In particular embodiments, the reactive group Rag may comprise a leaving group which is replaced by a portion of the nucleoside moiety as a result of the reaction.

The reactive group typically is a phosphorus derivative capable of coupling to a reactive site hydroxyl of a nucleoside moiety (e.g. on a nascent polynucleotide molecule in the process of being synthesized). A reactive group that is a phosphorus derivative has the structure (Vd)

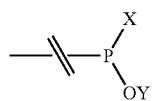

(Vd)

Wherein the groups are defined as follows:

The broken line indicates the bond to the sugar group, typically through either the 3'-O or 5'-O of the sugar group, though other suitable sites on the sugar group may serve to bond to the reactive group, particularly when the sugar group is other than a pentose.

X may be a halogen (particularly Cl or Br) or a secondary amino group, NQ1Q2. Preferred phosphorus derivatives are phosphoramidites, where X is NQ1Q2, and in which Q1 and Q2 may be the same or different and are typically selected from the group consisting of alkyl, aryl, aralkyl, cycloalkyl, alkenyl, cycloalkenyl, alkynyl, cycloalkynyl, optionally containing one or more nonhydrocarbyl linkages such as ether linkages, thio linkages, oxo linkages, amine, azole, and imine linkages, and optionally substituted on one or more available carbon atoms with a nonhydrocarbyl substituent such as cyano, nitro, halo, or the like. Typically, Q1 and Q2 represent lower alkyl, more preferably sterically hindered lower alkyls such as isopropyl, t-butyl, isobutyl, sec-butyl, neopentyl, tert-pentyl, isopentyl, sec-pentyl, and the like. More typically, Q1 and Q2 both represent isopropyl. Alternatively, Q1 and Q2 may be linked to form a mono- or polyheterocyclic ring having a total of from 1 to 3, usually 1 to 2 heteroatoms and from 1 to 3 rings. In such a case, Q1 and Q2 together with the nitrogen atom to which they are attached represent, for example, pyrrolidone, morpholino or piperidino. Usually, Q1 and Q2 have a total of from 2 to 12 carbon atoms. Examples of specific —NQ1Q2 moieties thus include, but are not limited to, dimethylamine, diethylamine, diisopropylamine, dibutylamine, methylpropylamine, methylhexylamine, methylcyclopropylamine, ethylcyclohexylamine, methylbenzylamine, methylcyclohexylmethylamine, butylcyclohexylamine, morpholine, thiomorpholine, pyrrolidine, piperidine, 2,6-dimethylpiperidine, piperazine, and the like.

Y is typically hydrido or hydrocarbyl (including substituted hydrocarbyl), typically alkyl, alkenyl, aryl, aralkyl, or cycloalkyl. More typically, Y represents: lower alkyl; benzyl; substituted benzyl; electron-withdrawing β-substituted aliphatic, particularly electron-withdrawing β-substituted ethyl such as β-trihalomethyl ethyl, β-cyanoethyl, β-sulfoethyl, β-nitro-substituted ethyl, and the like; electron-withdrawing substituted phenyl, particularly halo-, sulfo-, cyano- or nitro-substituted phenyl; or electron-withdrawing substituted phenylethyl. Still more typically, Y represents methyl, β-cyanoethyl, methyl-β-cyanoethyl, dimethyl-β-cyanoethyl, phenylsulfonylethyl, methyl-sulfonylethyl, p-nitrophenylsulfonylethyl, 2,2,2-trichloro-1,1-dimethylethyl, 2-(4-pyridyl)ethyl, 2-(2-pyridyl)ethyl, allyl, 4-methylene-1-acetylphenol, β-thiobenzoylethyl, 1,1,1,3,3,3-hexafluoro-2-propyl, 2,2,2-trichloroethyl, p-nitrophenylethyl, p-cyanophenyl-ethyl, 9-fluorenylmethyl, 1,3-dithionyl-2-methyl, 2-(trimethylsilyl)ethyl, 2-methylthioethyl, 2-(diphenylphosphino)-ethyl, 1-methyl-1-phenylethyl, 3-buten-1-yl, 4-(trimethylsilyl)-2-buten-1-yl, cinnamyl, α-methylcinnamyl, and 8-quinolyl.

Still referring to structure (IVd), the hydroxylprotecting group (e.g. on either the 3'-O or 5'-O, that is, designated by one of R2 or R3, respectively) is any suitable protecting group that is known to be releasable under conditions of simultaneous deprotection and oxidation during the polynucleotide synthesis cycle. Exemplary protecting groups that may be released to free the hydroxyl group during the simultaneous deprotection and oxidation step are described in U.S. Pat. No. 6,222,030 to Dellinger et al.; U.S. Pat. Appl'n Publ'n No. US2002/0058802 A1 to Dellinger et al.; and Seio et al. (2001) Tetrahedron Lett. 42 (49):8657-8660. In certain embodiments, the protecting groups may be carbonate protecting groups as described in U.S. Pat. No. 6,222,030. In some embodiments, the protecting groups may be aryl carbonate protecting groups as described in U.S. Pat. No. 6,222,030. In other embodiments, the protecting groups may be non-carbonate protecting groups as described in U.S. Pat. Appl'n Publ'n No. US2002/0058802 A1, such as for example, 3'- or 5'-O-silyl or -siloxyl protecting groups, 3'- or 5'-O-ester protecting groups, and 3'- or 5'-O-carbamate protecting groups. The hydroxylprotecting group may be, for example, a protecting group which is labile under nucleophilic attack under neutral or mildly basic conditions. Examples of protecting groups which are labile under nucleophilic attack under neutral or mildly basic conditions are: ester protecting groups, carbamate protecting groups, siloxane protecting groups, silane protecting groups, and sulfonate protecting groups that β-eliminate. Examples of suitable hydroxylprotecting groups for one of R2 or R3 in structure (IVd) are described in "Protective Groups in Organic Synthesis" by T. W. Green, Wiley Interscience.

With regard to the description of R2 and R3 of structure (IVd), it is well known within the art that synthesis of a polynucleotide may typically be performed in a 3' to 5' direction, or, alternatively, in the 5' to 3' direction. It will be apparent from the description herein given ordinary knowledge in the art that the hydroxylprotecting group and the reactive group designated by R2 and R3 may occupy either the 5'-O or 3'-O positions as described above. The synthesis and use of such alternate embodiments will be readily apparent given the skill in the art and the disclosure herein.

The Base group referenced in both structure (IId) and in structure (IVd) may be any heterocyclic base, e.g. purine and pyrimidine bases and analogs thereof. Typical examples of heterocyclic bases include the naturally occurring purine and pyrimidine bases, e.g., adenine (A), thymine (T), cytosine (C), guanine (G), or uracil (U), as well as modified purine and pyrimidine bases and other heterocyclic bases which have been modified (these moieties are sometimes referred to herein, collectively, as "purine and pyrimidine bases and analogs thereof"). Any heterocyclic base known in the literature of nucleotide analogs forms the basis for the Base group referenced in structure (IId) or structure (IVd). Typical examples include adenine, cytosine, guanine, thymine, uracil, and common analogs as recited earlier herein. Certain nucleotide analogs that are contemplated in this context include those described in U.S. Pat. Appl'n Ser. No. 10/324,409 entitled "Method Of Producing Nucleic Acid Molecules With Reduced Secondary Structure", filed on Dec. 18, 2002, and also those described in U.S. Pat. Appl'n Ser. No. 09/358,141 entitled "Method Of Producing Nucleic Acid Molecules With Reduced Secondary Structure", filed on Jul. 20, 1999. In particular embodiments, the Base group may include a protecting group, as is commonly known in the art of polynucleotide synthesis.

The Base group is typically bound by an N-glycosidic linkage to the 1' carbon of the sugar group, although other configurations are to be encompassed by the invention. In other embodiments, the Base group is bound by a C-glycosidic linkage to the 1' carbon of the sugar group. In some embodiments the Base group is bound to a carbon other than the 1' carbon of the sugar group. Other positions of the Base group on the sugar group and other linkages between the Base group and the sugar group may be practiced by those of skill in the synthesis of nucleotide analogs given the disclosure herein, especially where analogous structures having the given heterocyclic base and sugar group are known in the art.

In certain embodiments, the precursor may be e.g. a portion of an oligonucleotide or polynucleotide, a portion of a di-, tri-, tetra-, or penta-nucleotide (a small polynucleotide having 2, 3, 4, or 5 nucleotide monomer subunits). In such embodiments, the precursor typically has the structure (IId) described above, provided that the Sugar group is attached to a nucleotide moiety, an oligonucleotide moiety, or a polynucleotide moiety, in which the attached nucleotide moiety, oligonucleotide moiety, or polynucleotide moiety may have appropriate protecting groups. For example, the precursor may be a di- or tri-nucleotide in which the 3' or 5' hydroxyl bears a hydroxylprotecting group that is removed during the deprotection/oxidation step.

Certain embodiments in accordance with the present invention provide novel methods for synthesis of polynucleotides. Such methods involve forming an internucleotide bond by contacting a functionalized support having the structure (Id)

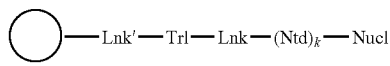 (Id)

with a precursor having the structure (IId)

Rag-Sugar-Base                         (IId)

under conditions and for a time sufficient to result in internucleotide bond formation.

In particular embodiments, the reactive group reacts with the available reactive site hydroxyl of the nucleoside moiety to result in the internucleotide bond being formed between the nucleoside moiety of the functionalized support and the sugar group of the precursor. In an embodiment, the method of synthesizing polynucleotides further includes, after the internucleotide bond is formed, exposing the result of the forming an internucleotide bond step to a composition which concurrently oxidizes the internucleotide bond and removes a hydroxylprotecting group from the Sugar group.

The functionalized support comprises a nucleoside moiety having a reactive site hydroxyl, a triaryl methyl linker group, and a solid support, the nucleoside moiety attached to the solid support via the triaryl methyl linker group.

The functionalized support employed in the current invention typically has the structure (Id)

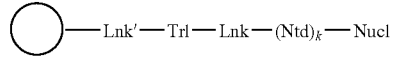 (Id)

Wherein the groups are defined as follows:

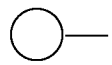

is a solid support,

Trl- is the triaryl methyl linker group, the triaryl methyl linker group having three aryl groups, each of the three aryl groups bound to a central methyl carbon, at least one of said three aryl groups having one or more substituents, Lnk'- is a linking group linking the solid support and the triaryl methyl linker group, or is a bond linking the solid support and the triaryl methyl linker group, $(Ntd)_k$- is a polynucleotide moiety having k nucleotide sub-units, wherein k is an integer in the range from zero to about 200, Lnk- is a linking group linking the triaryl methyl linker group and the polynucleotide moiety, or is a bond linking the triaryl methyl linker group and polynucleotide moiety, and Nucl- is a nucleoside moiety having a reactive site hydroxyl.

The solid support may comprise any suitable material adapted for its intended use in polynucleotide synthesis. The solid support should be essentially inert to the conditions of reactions used for the polynucleotide synthesis. Typically the solid support includes a solid substrate having a surface to which the triaryl methyl linker group is bound, directly or indirectly (i.e. via an intermediate moiety or moieties, e.g. moieties typically referred to in the art variously as linking groups (e.g. the Lnk'- group), tethers, or spacers; further e.g. a modification layer on the surface), to the surface. The triaryl methyl linker group is attached to the solid support via a bond to one of the aromatic rings of the triaryl methyl linker group, that is, the solid support (and any intermediate moieties, e.g. the Lnk'- group) may be considered a substituent of one of the aromatic rings. As indicated in structure (Id), the nucleoside moiety is attached to the solid substrate via the triaryl methyl linker group such that the nucleoside moiety is accessible to the precursor when the functionalized support is contacted with a solution containing the precursor.

In certain embodiments, the solid support comprises a solid substrate and a modification layer disposed on (or bound to, directly or indirectly) the substrate, and the triaryl methyl linker group is bound to (directly or indirectly) the modification layer. Such modification layer may be formed on the substrate by methods known in the art of modifying surface properties of supports used in polynucleotide synthesis, or known in the art of modifying supports to provide desired surface properties. In certain embodiments, the modification layer may be, e.g. a coating, a material deposited by deposition techniques known in the art, a hydrophobic layer, or a hydrophilic layer. In particular embodiments, the modification layer comprises a silane group to which the triaryl methyl linker group is bound, directly or indirectly, e.g. via any linking group effective to link the triaryl methyl linker group to the silane group and stable to the conditions used in polynucleotide synthesis. Particularly contemplated are supports taught in U.S. Pat. No. 6,258,454 to Lefkowitz et al. (2001) as supports having a moiety bound to a substrate via a linking group attached to a silane group bound to the surface of a substrate.

Functionalized supports in accordance with the present invention may be made using silane modified substrates such as are employed in the Lefkowitz '454 patent and modifications thereof. A functional group attached (directly or indirectly, e.g. via a linking group) to the silane group on the substrate provides a site for further attachment to the substrate to occur. The substrate bearing the functional group is then contacted with a composition having a surface-binding group attached to a triaryl methyl linker group. The surface-binding group is capable of reacting with the functional group attached to the substrate to result in attachment of the triaryl methyl linker group to the solid support. Of course, other moieties, such as a nucleoside moiety, attached to the triaryl methyl linker group will thusly also be attached to the solid support. The resulting functionalized support may then be used in polynucleotide synthesis. The functional group attached to the substrate will typically be selected from amine, hydroxyl, sulfhydryl, carboxyl, carbonyl, phosphate and thiophosphate, and combinations thereof. The surface-binding group comprises a group that is chemically reactive with (and forms a covalent bond with) the functional group attached to the substrate. The surface-binding group will typically be selected from succinimidyl ester, isothiocyanate, isocyanate, haloacetamide, dichlorotriazine, maleimide, sulphonyl halide, alkylimidoester, arylimidoester, substituted hydrazine, substituted hydroxylamine, carbodiimide, acyl halide, anhydride, phosphoramidite, acrylate and acrylamide. Selection of an appropriate surface-binding group will be based on the identity of the functional group attached to the substrate, and vice versa. Such selection is within the skill of those in the art given the disclosure herein.

The solid substrate typically comprises a material that is stable to conditions used in the synthesis of polynucleotides; such materials include, but are not limited to, supports that are typically used for solid-phase chemical synthesis, e.g. cross-linked polymeric materials (e.g. divinylbenzene styrene-based polymers), agarose (e.g. SEPHAROSE media), dextran (e.g. SEPHADEX media), cellulosic polymers, polyacrylamides, silica, glass (such as controlled pore glass "CPG"), ceramics, and the like.

Referring to structure (Id), the Trl- group is a substituted triaryl methyl linker group and has the structure (VId),

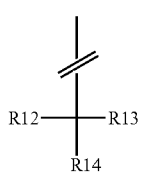

(VId)

wherein the broken line represents a bond via which the rest of the structure (VId) is connected to the nucleoside moiety (e.g. via the polynucleotide moiety), and R12, R13, and R14 are independently selected from aromatic ring moieties, each aromatic ring moiety comprising 4-, 5-, or 6-membered rings, provided that one of R12, R13, or R14 is substituted by being bonded to the solid support. Each aromatic ring moiety can independently be heterocyclic, non-heterocyclic, polycyclic or part of a fused ring system. Each aromatic ring moiety can be unsubstituted or substituted with one or more groups each independently selected from the group consisting of lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl thio, mercapto, amino, imino, halo, cyano, nitro, nitroso, azido, carboxy, sulfide, sulfone, sulfoxy, phosphoryl, silyl, silyloxy, and boronyl; provided that, as noted above, one of R12, R13, and R14 is substituted by being bound to the solid support, e.g. via a covalent bond between the ring and a surface modification layer of the solid support, or further e.g. via a covalent bond between a linking group attached to the ring and a functional group of the solid support. Typical triaryl methyl groups that may be employed in embodiments herein are described in U.S. Pat. No. 4,668,777 to Caruthers, again provided that, as noted above, one of R12, R13, and R14 is substituted by being bound to the solid support; use of such groups in accordance with the present invention is within ordinary skill in the art given the disclosure herein. A substituted triaryl methyl group may have one substituent (i.e. a singly substituted triaryl methyl group) on one of the aromatic rings of the triaryl methyl group, or may have multiple substituents (i.e. a multiply substituted triaryl methyl group) on one or more of the aromatic rings of the triaryl methyl group. As used herein, an aromatic ring moiety may be referenced as an "aromatic ring structure". As used herein, the "central methyl carbon" of a triaryl methyl group is the carbon bonded directly to the three aromatic ring structures.

In certain embodiments, R12 and R13 are each independently selected from substituted or unsubstituted aromatic groups such as phenyl, biphenyl, naphthanyl, indolyl, pyridinyl, pyrrolyl, thiophenyl, furanyl, annulenyl, quinolinyl, anthracenyl, and the like, and R14 is selected from substituted aromatic groups such as phenyl, biphenyl, naphthanyl, indolyl, pyridinyl, pyrrolyl, thiophenyl, furanyl, annulenyl, quinolinyl, anthracenyl, and the like. In some embodiments, at least one of R12, R13 and R14 is selected from substituted or unsubstituted aromatic groups other than phenyl such as naphthanyl, indolyl, pyridinyl, pyrrolyl, furanyl, annulenyl, quinolinyl, anthracenyl, and the like; in such embodiments zero, one, or two of R12, R13, and R14 are selected from substituted or unsubstituted phenyl, provided that, as noted above, one of R12, R13, and R14 is substituted by being bound (e.g. through Lnk') to the solid support.

In some embodiments, R12, R13, and R14 are independently selected from structure (VIId).

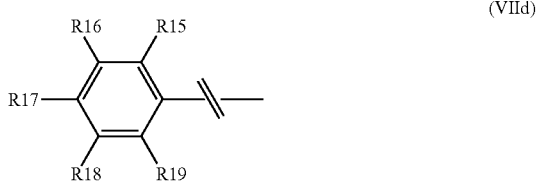

(VIId)

In structure (VIId), the broken line represents the bond to the central methyl carbon of the triaryl methyl linker group, and R15, R16, R17, R18, and R19 are each independently selected from hydrido, lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl, provided that, for R14, one of the groups R15, R16, R17, R18, and R19 denotes the linkage to the solid support, or is the group via which the triaryl methyl linker group is attached to the solid support (e.g. through Lnk').

In particular embodiments, R12, R13, and R14 are each independently selected from phenyl, methoxyphenyl, dimethoxyphenyl, and trimethoxyphenyl groups, such that the Trl- group of structure (Id) may be a trityl group, a monomethoxytrityl group, a dimethoxytrityl group, a trimethoxytrityl group, a tetramethoxytrityl group, a pentamethoxytrityl group, a hexamethoxytrityl group and so on; again provided as described above that one of R12, R13, and R14 is substituted by being bound to the solid support.

In particular embodiments, R12, R13, and R14 are each independently selected from phenyl, methoxyphenyl groups, dimethoxyphenyl groups, trimethoxyphenyl groups, tetramethoxyphenyl groups, pentamethoxyphenyl groups, or furyanyl groups such that the Trl- group of structure (Id) may be a substituted trityl group, a monomethoxytrityl group, a dimethoxytrityl group, a trimethoxyl trityl group, a tetramethoxy trityl group, a pentamethoxytrityl group, an anisylphenylfuranylmethyl group, a dianisylfuranylmethyl group, a phenyldifuranylmethyl group, an anisyldifuranylmethyl group or a trifuranylmethyl group, again provided as described above that one of R12, R13, and R14 is substituted by being bound to the solid support.

Referring to structure (Id), $(Ntd)_k$- is a polynucleotide moiety having k nucleotide sub-units, wherein k is an integer typically in the range from zero to about 200, more typically in the range from about 1 to about 200, still more typically in the range from about 2 to about 200, still more typically in the range from about 5 to about 200. It will be apparent that during the initial steps of polynucleotide synthesis, k may be zero or one, and that as the synthesis cycle is repeated, k will get larger. In certain embodiments, k may be up to 60, more typically up to 100, still more typically up to 200, or even more. The polynucleotide moiety typically may include naturally occurring and/or non-naturally occurring heterocyclic bases and may include heterocyclic bases which have been modified, e.g. by inclusion of protecting groups or any other modifications described herein, or the like. As used herein, "polynucleotide moiety" references a series of connected nucleotide subunits that is a portion of a larger molecule. The polynucleotide moiety is typically bound to the linking group via a 3'-O— or a 5'-O— of the polynucleotide moiety, although other sites of the polynucleotide moiety are contemplated and are within the scope of the invention. The polynucleotide moiety is typically bound to the Nucl- group via a 3'-O— or a 5'-O— of the polynucleotide moiety, although other sites of the polynucleotide moiety are contemplated and are within the scope of the invention. Use of such other sites of the polynucleotide moiety by which the polynucleotide moiety may be bound to the linking group or the Nucl- group are within the skill in the art given the disclosure herein.

Still referring to structure (Id), the Lnk- group is selected from (1) a linking group linking the central methyl carbon of the triaryl methyl linker group to the polynucleotide moiety (typically at the 5' or 3' terminal hydroxyl, or other suitable site of the polynucleotide moiety), or (2) a covalent bond between the central methyl carbon of the triaryl methyl linker group and the polynucleotide moiety (e.g. at the 5' or 3' terminal hydroxyl, or other suitable site of the polynucleotide moiety). In particular embodiments, the Lnk- group may be any appropriate linking group that links the triaryl methyl linker group to the polynucleotide moiety, the linking group typically selected from (1) a lower alkyl group; (2) a modified lower alkyl group in which one or more linkages selected from ether-, oxo-, thio-, amino-, and phospho- is present; (3) a modified lower alkyl substituted with one or more groups including lower alkyl; aryl, aralkyl, alkoxyl, thioalkyl, hydroxyl, amino, sulfonyl, halo; or (4) a modified lower alkyl substituted with one or more groups including lower alkyl; alkoxyl, thioalkyl, hydroxyl, amino, sulfonyl, halo, and in which one or more linkages selected from ether-, oxo-, thio-, amino-, and phospho- is present. In certain embodiments, the linking group is a single non-carbon atom, e.g. —O—, or a single non-carbon atom with one or more hydrogens attached, e.g. —N(H)—.

Still referring to structure (Id), the Lnk'- group is selected from (1) a linking group linking the solid support and the triaryl methyl linker group (typically Lnk'- is bound to a ring atom of one of the aryl groups of the triaryl methyl linker group, i.e. the Lnk'- group may be considered a substituent of one of the aryl groups of the triaryl methyl linker group); or (2) a covalent bond between the solid support and the triaryl methyl linker group (e.g. the solid support is bound to a ring atom of one of the aryl groups of the triaryl methyl linker group, i.e. the solid support may be considered a substituent of one of the aryl groups of the triaryl methyl linker group). In particular embodiments, the Lnk'- group may be any appropriate linking group that links the triaryl methyl linker group to the solid support, the linking group typically selected from (1) a lower alkyl group; (2) a modified lower alkyl group in which one or more linkages selected from ether-, oxo-, thio-, amino-, and phospho- is present; (3) a modified lower alkyl substituted with one or more groups including lower alkyl; aryl, aralkyl, alkoxyl, thioalkyl, hydroxyl, amino, sulfonyl, halo; or (4) a modified lower alkyl substituted with one or more groups including lower alkyl; alkoxyl, thioalkyl, hydroxyl, amino, sulfonyl, halo, and in which one or more linkages selected from ether-, oxo-, thio-, amino-, and phospho- is present. In certain embodiments, the Lnk'- group is a single non-carbon atom, e.g. —O—, or a single non-carbon atom with one or more hydrogens attached, e.g. —N(H)—. In one embodiment, the Lnk'- group has the structure —O—R28—NH—C(O)—NH—, wherein the R28 group is selected from hydrocarbyl, substituted hydrocarbyl, and modified alkyl; in particular embodiments, R28 is lower alkyl or modified lower alkyl. In embodiments in which the Lnk'- group has the structure —O—R28—NH—C(O)—NH—; the terminal oxygen "—O" of the Lnk'- group will typically be bound directly to an aromatic group of the triaryl methyl linker group, and the terminal nitrogen "NH—" of the Lnk'- group will typically be the group via which the rest of the Lnk'- group is attached to the solid support.

Again referring to structure (Id), the Nucl- group is a nucleoside moiety having a reactive site hydroxyl. The nucleoside moiety is attached to the solid support via a triaryl methyl linker group. The nucleoside moiety has a sugar group (the sugar group comprising the reactive site hydroxyl) and a heterocyclic base. The sugar group of the nucleoside moiety may be any sugar group described above with reference to the precursor of structure (IId), provided that, instead of being bonded to the reactive group (of structure (IId)), the sugar group is bound to the solid support (via the triaryl methyl linker group, and also via the intervening Lnk- and $(Ntd)_k$- groups in the embodiments depicted by structure (Id)); further provided that the reactive site hydroxyl is not protected by a protecting group (although other sites on the sugar group may optionally bear protecting groups). In use, the reactive site hydroxyl typically originates from the immediately preceding iteration of the synthesis cycle, in which the deprotection/oxidation step results in the deprotection of a hydroxyl that is then available to be the reactive site hydroxyl in the next iteration of the synthesis cycle. The heterocyclic base of the nucleoside moiety may be selected from the naturally occurring purine and pyrimidine bases, e.g., adenine (A), thymine (T), cytosine (C), guanine (G), or uracil (U), or modified purine and pyrimidine bases and other heterocyclic bases which have been modified. The heterocyclic base of the nucleoside moiety may include a protecting group, or may lack any protecting group. The heterocyclic base is typically bound by an N-glycosidic linkage to the 1' carbon of the sugar group, although other configurations are to be encompassed by the invention. In other embodiments, the heterocyclic base is bound by a C-glycosidic linkage to the 1' carbon of the sugar group. In some embodiments the heterocyclic base is bound to a carbon other than the 1' carbon of the sugar group. Other positions of the heterocyclic base (the atom of the heterocyclic base ring via which the heterocyclic base is linked to the sugar group) and other linkages between the heterocyclic base and the sugar group may be practiced by those of ordinary skill in the synthesis of nucleotide analogs given the disclosure herein, especially where analogous structures having the given heterocyclic base and sugar group are known in the art. The Nucl- group is typically bound to the polynucleotide moiety via a 3'-O— or a 5'-O— of the Nucl- group, although other sites of the Nucl- group are contemplated and are within the scope of the invention. Use of such other sites of the Nucl- group by which the Nucl- group may be bound to the polynucleotide moiety are within the skill in the art given the disclosure herein.

In accordance with the invention, a functionalized support suitable for use in polynucleotide synthesis is provided, wherein the functionalized support comprises a nucleoside moiety bound to a surface of the solid support via a triaryl methyl linker group. The functionalized support may then be used to perform polynucleotide synthesis. In a method for synthesis of a polynucleotide, the functionalized support is contacted with a precursor having the structure (IId) under conditions and for a time sufficient to allow the precursor to react with an available reactive site hydroxyl group of the nucleoside moiety. Such reactions in accordance with the invention described herein may be repeated a plurality of times to result in the synthesized polynucleotide bound to the surface via a triaryl methyl linker group.

Figure 3:
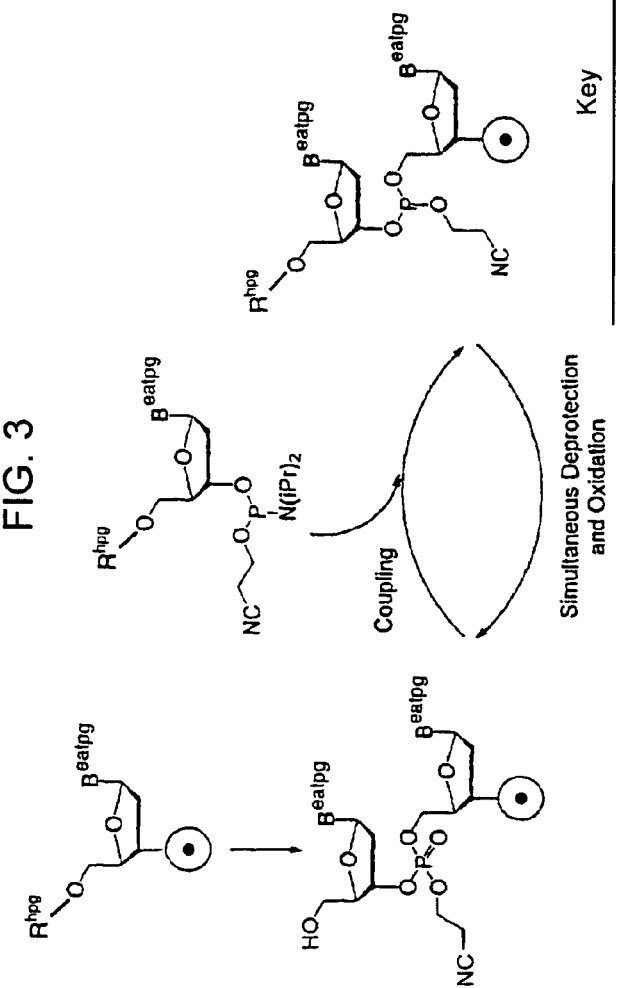
FIG. 3 shows a method of synthesis of polynucleotides according to the present invention.

In use, a precursor that has the structure (IId) is contacted with a reactive site hydroxyl of a nucleoside moiety to result in formation of an internucleotide bond. Such a reaction is generally shown in FIG. 3, as discussed further, below. FIG. 3 schematically illustrates 3'-to-5' synthesis of a polynucleotide using the method of the present invention. In FIG. 3, the

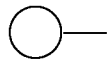

symbol represents the functionalized support as described herein with respect to structure (Id) except the Nucl group, which is explicitly drawn in the figure. That is, the

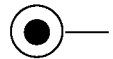

symbol represents

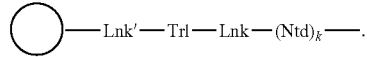

Figure 2:
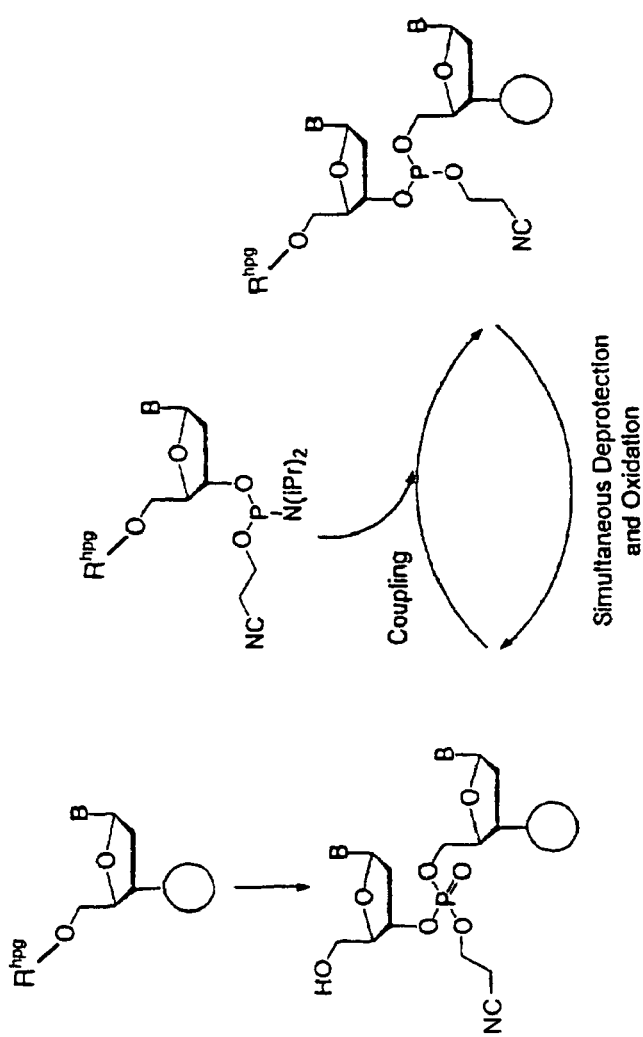
FIG. 2 depicts a synthesis scheme employing a two step synthesis cycle, including a coupling step and a simultaneous deprotection and oxidation step.

In the figure, the moiety $R^{hpg}$ represents a hydroxylprotecting group releasable under conditions of simultaneous deprotection and oxidation during the polynucleotide synthesis cycle, as further described herein. In FIG. 3, —B represents a Base group as described herein. As may be seen, in the second step of the synthesis cycle, deprotection and oxidation occur concurrently. The synthesis may be contrasted with that schematically illustrated in FIG. 1, the prior, conventional method, where the conventional synthesis scheme entails separate oxidation and deprotection steps. The synthesis also may be contrasted with that schematically illustrated in FIG. 2, showing a synthesis with the previously taught starting materials. Such a synthesis scheme is known in the art, such as that taught in, e.g. U.S. Pat. No. 6,222,030 to Dellinger et al.; U.S. Pat. Appl'n Publ'n No. US2002/0058802 A1 to Dellinger et al.; Seio et al. (2001) Tetrahedron Lett. 42 (49): 8657-8660. These references describe two-step methods of (1) coupling a hydroxyl-protected nucleoside monomer to a growing oligonucleotide chain, and (2) deprotecting the product using an alpha effect nucleophilic reagent that also oxidizes the internucleotide linkage to give a phosphotriester bond. The coupling and deprotection/oxidation steps are repeated as necessary to give an oligonucleotide having a desired sequence and length.

The invention further provides a method for synthesizing polynucleotides. In an embodiment, the method comprises forming an internucleotide bond by contacting a functionalized support having the structure (Id) with a precursor having the structure (IId) as described above under conditions and for a time sufficient to allow the precursor to react with the nucleoside moiety of the functionalized support to result in formation of the internucleotide bond. In particular embodiments, the method comprises forming an internucleotide bond by contacting a functionalized support having the structure (Id) with a precursor having the structure (IVd) as described above under conditions and for a time sufficient to allow the precursor to react with the nucleoside moiety of the functionalized support to result in formation of the internucleotide bond. The nucleoside moiety typically comprises a reactive site hydroxyl that is capable of reacting with the reactive group of the precursor to result in formation of an internucleotide bond.

In an embodiment, the method of synthesizing polynucleotides further includes, after the internucleotide bond is formed, exposing the result of the forming an internucleotide bond step to a composition which concurrently oxidizes the internucleotide bond and removes a hydroxylprotecting group (the simultaneous deprotection and oxidation step).

In an embodiment of the method for 3' to 5' synthesis, a precursor having the structure (IVd) as described above is contacted with a nucleoside moiety of a functionalized support having the structure (VIId):

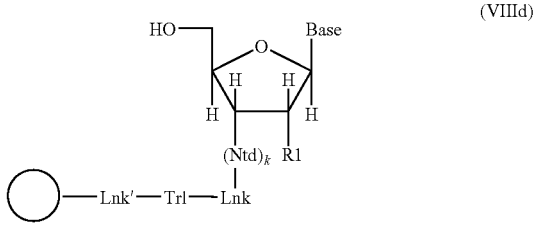

(VIIId)

Wherein the groups are defined as follows:

Base is a heterocyclic base, optionally protected with a protecting group

is a solid support, and

R1, Lnk', Trl, Lnk, and $(Ntd)_k$ are each as described above.

The nucleoside moiety of structure (VIIId) has a reactive site hydroxyl that is available to react with the reactive group of a precursor. The coupling reaction is performed under conditions and for a time sufficient to allow the precursor to react with the nucleoside moiety to result in formation of the internucleotide bond. The product of the coupling reaction may be represented as structural formula (IXd), as follows:

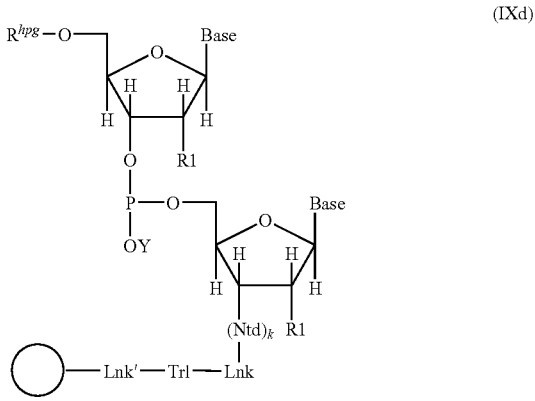

(IXd)

Wherein the groups are defined as follows:

is a solid support, $R^{hpg}$ represents a hydroxylprotecting group releasable under conditions of simultaneous deprotection and oxidation during the polynucleotide synthesis cycle, Each R1 is independently as described above with regard to structure (IVd), Each Base is independently as described above with regard to structure (IVd), Y, Lnk', Trl, Lnk, and $(Ntd)_k$ are each as described above.

In FIG. 3, this step (the "coupling" reaction) is illustrated in context of a full synthesis cycle. The coupling reaction may be conducted under standard conditions used for the synthesis of oligonucleotides and conventionally employed with automated oligonucleotide synthesizers. Such methodology will be known to those skilled in the art and is described in the pertinent texts and literature, e.g., in D. M. Matteuci et al. (1980) Tet. Lett. 521:719 and U.S. Pat. No. 4,500,707.

It will be apparent to the skilled reader that, for polynucleotide synthesis, different bases may be employed each synthesis cycle depending on the desired sequence of the final product. Synthesis of polynucleotides having such desired sequences is within the scope of the invention, as implied by the Base group in structure (IXd).

In the second step of the synthesis cycle shown in FIG. 3, the product is treated with a combined deprotection/oxidation reagent to oxidize the newly formed internucleotide bond and to remove the hydroxylprotecting group at the 5' terminus, thus converting the moiety —$OR^{hpg}$ to —OH. The resulting —OH is then available to serve as the reactive site hydroxyl for the next round of the synthesis cycle. Advantageously, the combined deprotection/oxidation step may be conducted in connection with fluorescent or other readily detectable hydroxylprotecting groups, enabling monitoring of individual reaction steps. Further, the method is useful in carrying out either 3'-to-5' synthesis or 5'-to-3' synthesis. Finally, the method readily lends itself to the highly parallel, microscale synthesis of oligonucleotides.

The deprotection/oxidation reaction essentially may be conducted under the reported conditions used for the synthesis of polynucleotides as described in, e.g. U.S. Pat. No. 6,222,030 to Dellinger et al.; U.S. Pat. Appl'n Publ'n No. US2002/0058802 A1 to Dellinger et al.; Seio et al. (2001) Tetrahedron Lett. 42 (49):8657-8660. As will be appreciated by those of ordinary skill in the art, given the disclosure herein, the conditions for the deprotection/oxidation step may vary depending on the nature of the protecting groups used. In order to be compatible with the triaryl methyl linker group provided for by the current invention, the conditions for the simultaneous deprotection and oxidation step (i.e. required conditions for release of the hydroxylprotecting group) should be selected such that the nascent polynucleotide remains attached to the soluble support via the triaryl methyl linker group. Typical conditions for the deprotection/oxidation reaction include a pH in the neutral to moderately basic range. In particular embodiments, the pH of the deprotection/oxidation reaction is at least about 6.0, typically at least about 6.5, more typically at least about 7.0, still more typically at least about 7.5, and the pH is typically less than about 12, typically less than about 11, more typically less than about 10.5, still more typically less than about 10.

The combined deprotection/oxidation reagent may be selected to provide particularly advantageous synthesis conditions and characteristics, as are described herein. In an embodiment, the combined deprotection/oxidation reagent provides for contacting of the elongating polynucleotide chain with an alpha effect nucleophile under neutral or mildly basic aqueous conditions to remove reactive site hydroxylprotecting groups where such protecting groups are labile under nucleophilic attack; the alpha effect nucleophile also serves to oxidize the phosphite triester linkage to a phosphotriester linkage.

In an embodiment, the combined deprotection/oxidation reagent provides a nucleophilic deprotection reagent under neutral or mildly basic conditions in aqueous solution. During the second step of the polynucleotide synthesis cycle (the deprotection/oxidation step in FIG. 3), the product is treated with an "alpha effect" nucleophile in order to remove the protecting group at the reactive site hydroxyl (e.g. the 5' terminus), thus converting the moiety —OR$^{hpg}$ to —OH. The alpha effect nucleophile also oxidizes the newly formed phosphite triester linkage to give the phosphotriester linkage as shown in FIG. 3.

The deprotection/oxidation reagent may be any compound or mixture of compounds that is compatible with the synthesis of polynucleotides and has the properties discussed herein. Typically, the deprotection/oxidation reagent includes a concentration of an oxidant that is high enough to rapidly oxidize the newly formed phosphite internucleotide linkage. This is typically at least 0.1% vol/vol, typically at least 0.5% vol/vol, more typically at least about 1.0% vol/vol, still more typically at least about 3.0% vol/vol. The concentration of the oxidant typically should be low enough to avoid appreciable (e.g. less than 1% per iteration of the synthesis cycle) amounts of oxidative destruction of the nucleobases or protected nucleobases. This concentration is typically less than 10% vol/vol, more typically less than 9% vol/vol, still more typically less than 7% vol/vol.

The deprotection/oxidation reagent in typical embodiments provides a source of a peroxyanion at neutral to mildly basic pH in the reaction mixture during the deprotection/oxidation reaction. The concentration of the peroxyanion will be related to the acid dissociation constant of the hydroperoxide species at equilibrium. The concentration of peroxyanion is typically in the range 0.01% to 99% of the total hydroperoxide concentration (i.e. sum of all hydroperoxide species, e.g. protonated and unprotonated forms), more typically in the range 0.05% to 90% of the total hydroperoxide concentration, yet more typically in the range 0.1% to 50% of the total hydroperoxide concentration, still more typically in a range of 1.0% to 30% of the total hydroperoxide concentration.

In certain embodiments, the nucleophilic deprotection reagent that exhibits an alpha effect is a peroxide or a mixture of peroxides. In typical embodiments, the pH at which the deprotection/oxidation reaction is conducted is generally in the range of about three pH units below the pKa of the nucleophilic deprotection reagent (that is, the pKa for formation of the corresponding peroxy anion) up to about three pH units above the pKa of the nucleophilic deprotection reagent. More typically, the pH of the deprotection/oxidation reaction is in the range of about one pH unit below the pKa of the nucleophilic deprotection reagent up to about pH 11. Preferably the pH will be the range that allows a high enough concentration of the peroxy anion to form, e.g. from about the pKa of the peroxide up to a pH of about 11. The peroxide may be either inorganic or organic. Suitable inorganic peroxides include those of the formula M+OOH—, where M+ is any counter ion, including for example H+, Li+, Na+, K+, Rb+, Cs+, or the like; and lithium peroxide or hydrogen peroxide and alkaline stabilized forms thereof can be particularly suitable. Suitable organic peroxides include those of the formula ROOH, where R is selected from the group consisting of alkyl, aryl, substituted alkyl, substituted aryl, and modified alkyl. More particularly, the organic peroxide will have one of the following three general structures (Xd), (XId) or (XIId)

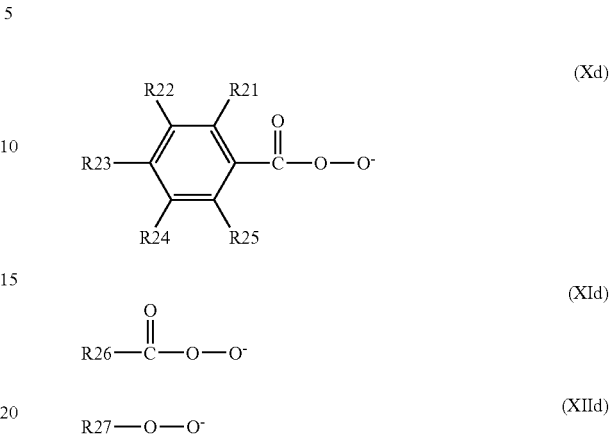

in which R21 through R27 are generally hydrocarbyl optionally substituted with one or more nonhydrocarbyl substituents and optionally containing one or more nonhydrocarbyl linkages. Generally, R21 through R27 are independently selected from the group consisting of hydrido, alkyl, modified alkyl, aryl, aralkyl, cycloalkyl, cycloalkylalkyl, alkenyl, cycloalkenyl, alkynyl aralkynyl, cycloalkynyl, substituted aralkyl, substituted cycloalkyl, substituted cycloalkylalkyl, substituted alkenyl, substituted cycloalkenyl, substituted alkynyl, substituted aralkynyl, substituted cycloalkynyl, hydrocarbyl, and substituted hydrocarbyl. T-butyl-hydroperoxide or metachloroperoxybenzoic acid can be particularly suitable. As a specific example, the m-chloroperoxybenzoic acid (mCPBA) peroxy anion has been found to be useful for removal of protecting groups on the reactive site hydroxyl.

As indicated in FIG. 3, the steps of the synthesis cycle include a coupling step and a simultaneous deprotection/oxidation step. In an embodiment of a method of synthesizing a polynucleotide in accordance with the present invention, these steps of the synthesis cycle may be repeated multiple times to produce a polynucleotide having the desired sequence.

The use of a triaryl methyl linker group provides for release of the synthesized polynucleotide from the solid support. In typical embodiments, the synthesized polynucleotide may be released from the solid support to yield the polynucleotide free in solution (not attached to the support). This reaction typically is conducted under mildly acidic conditions. In particular embodiments, the synthesized polynucleotide is cleaved from the triaryl methyl linker group by weak acids under conditions that do not result in destruction of the glycosidic linkage, typically glacial acetic acid or glacial acetic acid/water mixtures.

The functionalized support which is contacted with the precursor in the method of the present invention typically comprises a nucleoside moiety bound to a solid support directly or via an intervening polynucleotide strand. The solid support may comprise any suitable material adapted for its intended use in polynucleotide synthesis. The solid support should be essentially inert to the conditions of reactions used for the polynucleotide synthesis. Typically the solid support has a surface to which the nucleoside moiety (or a polynucleotide which comprises the nucleoside moiety) is bound, directly or indirectly (i.e. via an intermediate moiety or moieties, e.g. moieties typically referred to in the art variously as linking groups, tethers, or spacers); such that the nucleoside moiety, which has the reactive site hydroxyl, is accessible to the precursor when the functionalized support is contacted with a solution containing the precursor.

In certain embodiments, the solid support comprises a solid substrate and a modification layer disposed on or bound to (directly or indirectly) the substrate, and the nucleoside moiety having the reactive site hydroxyl is bound to (directly or indirectly) the modification layer. Such modification layer may be formed on the substrate by methods known in the art of modifying surface properties of supports used in polynucleotide synthesis, or known in the art of modifying supports to provide desired surface properties. In certain embodiments, the modification layer may be, e.g., a coating, a material deposited by deposition techniques known in the art, a hydrophobic layer, or a hydrophilic layer. In particular embodiments, the support comprises a chemically active group bound to a substrate via a silane group. Particularly contemplated are solid supports taught in U.S. Pat. No. 6,258, 454 to Lefkowitz et al. (2001) as solid supports having a chemically active moiety bound to a substrate via a linking group attached to a silane group bound to the surface of a substrate.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, percents are wt./wt., temperature is in ° C. and pressure is at or near atmospheric. Standard temperature and pressure are defined as 20° C. and 1 atmosphere.

Polynucleotide synthesis by the 2-step process previously described with regard to FIG. 2 and FIG. 3 typically includes the use of a linker that is stabile to the conditions used for the simultaneous deprotection/oxidation (second step). In accordance with the present invention, acid labile linking groups suitable for such use and supports functionalized with such linking groups are provided.

A synthesis of reagents used in certain embodiments of the present invention is now described. It will be readily apparent that the reactions described herein may be altered, e.g. by using modified starting materials to provide correspondingly modified products, and that such alteration is within ordinary skill in the art. Given the disclosure herein, one of ordinary skill will be able to practice variations that are encompassed by the description herein without undue experimentation.

Abbreviations used in the examples include: THF is tetrahydrofuran; TLC is thin layer chromatography; HEX is hexane; Et$_3$N is triethylamine; MW is molecular weight; AcCN is acetonitrile; sat'd is saturated; EtOH is ethanol; DCM is methylene chloride; EtOAc is ethyl acetate; MS is mass spectrometry; MS (ES) is mass spectrometry (electrospray); HRMS is high resolution mass spectrometry; and FAB is fast atom bombardment.

Example A

5'-O-(4-(3-(4-Nitrophenoxycarbonyl)-aminopropoxy)-4'-methoxytrityl)-2'-deoxythymidine is produced by the following protocol:

4-hydroxy-4'-methoxytrityl alcohol (Step 1)

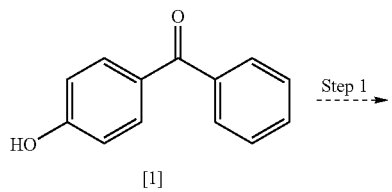

[1]
M.W. = 198.1

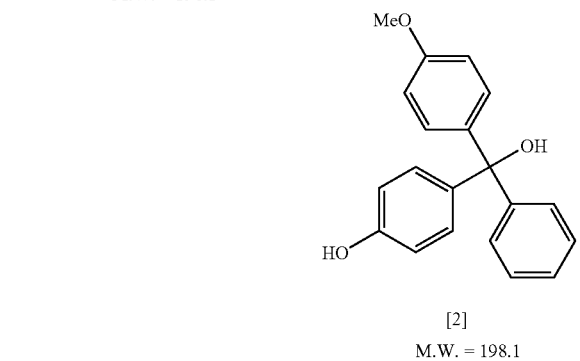

[2]
M.W. = 198.1

A. 25.0 g (126.2 mmoles) 4-hydroxy Benzophenone (1); Aldrich # H2020-2

B. 500 ml THF; Aldrich # 49446-1

C. 700 ml of a 0.5 M Solution in THF (175 mmoles) 4-Anisyl Magnesium Bromide; Alpha-Aesar # 89435

TLC System: HEX/EtOAc/Acetone (4:1:1)+0.5% Et$_3$N on silica gel

Using a 3-L 3-neck round bottom flask with a mechanical stirrer, U-tube thermometer and drying tube, (A) was added to (B) and the solution was cooled to 4° C. in a dry-ice/acetone bath, under Argon atmosphere. (C) was added drop wise over a period of 1 hour. Precipitate forms tan→pink color. The temperature was kept between 0-5° C. during the addition. The mixture was removed from the bath and stirred at ambient temperature (under Argon atmosphere) for 16-hours. The solvent was evaporated in vacuo. The residue was suspended in 300 ml ether and 200 mL cold water. The ether layer was extracted with 150 mL saturated NaHCO$_3$ and 150 mL saturated NaCl and dried with MgSO$_4$. The solvent was evaporated, and 66 g of an oily residue was obtained. The residue was dissolved in 50 mL DCM, 30 g silica gel added and column purified over silica gel, with DCM/AcCN (19:1) as the initial mobile phase, changing to DCM/AcCN (9:1) as mobile phase for elution of the product. The product was column purified a second time over silica gel using EtOAc/HEX (1:1) as mobile phase for elution of the product.

Theoretical Yield: 38.6 g

Actual Yield: 23.9 g [62%]

$^1$H NMR (CDCl$_3$) 3.78 (3H, s), 6.75 (2H, d, J=8.8), 6.83 (2H, d, J=8.8), 7.11 (2H, d, J=8.8), 7.17 (2H, d, J=8.8), 7.25-7.32 (5H, m); MS (ESI−) m/z 305 (M−1, 100); (ESI+) m/z 635 (M$_2$+Na, 33), 289 (M−H$_2$O, 100)

4-(3-phthalimidopropxy)-4'-methoxytrityl alcohol (Step 2)

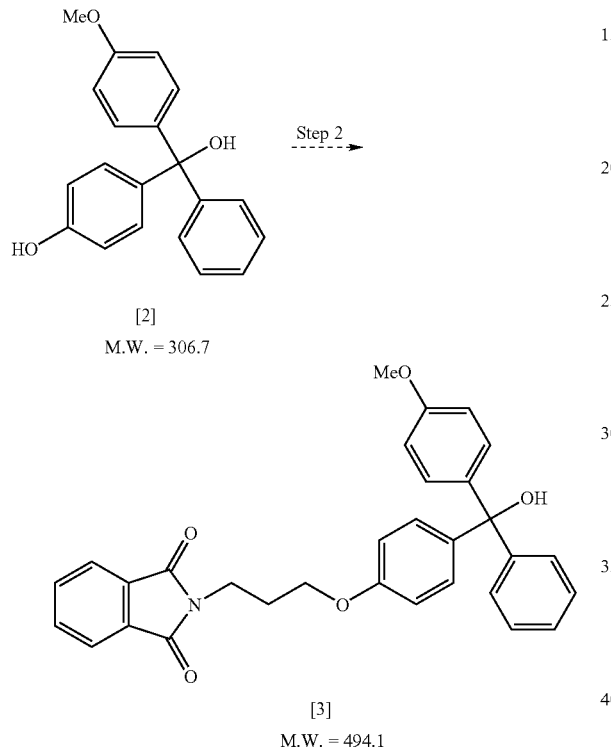

TLC System: DCM/AcCN [19:1]
A. 24.0 g (78.0 mmoles) [2]
B. 21.6 g (156 mmoles) potassium carbonate MW=138.1; Aldrich # 20961-9
C. 63 g (235 mmoles) 3-bromopropyl phthalamide MW=268.1; Aldrich # B8000-3
D. Single (Dry) Crystal Potassium Iodide MN 166.1; Aldrich # 22194-5
E. 600 mL Toluene Using a 2L 3-neck round bottom flask equipped with a thermometer, reflux condenser, drying tube and stir bar, (A), (B) (C), and (D) were added to (E) in sequential order. The mixture was heated to reflux for 24 hours. The solvent was evaporated. The residue was partitioned between 750 mL DCM and 300 mL water. The DCM layer was washed twice with 400 mL sat'd NaCl then dried over MgSO$_4$. The product was then column purified over a silica gel column packed with DCM and eluted with DCM/AcCN (19:1) as mobile phase.

Theoretical Yield: 38.5 g

Actual Yield: 20 g [52%]

$^1$H NMR (CDCl$_3$) 2.14-2.18 (2H, m), 2.91 (1H, s), 3.78 (3H, s), 3.87 (2H, t, J=7.0), 3.99 (2H, t, J=6.2), 6.71 (2H, d, J=8.8), 6.80 (2H, d, J=8.8), 7.10 (2H, d, J=8.8), 7.15 (2H, d, J=8.8), 7.23-7.28 (5H, m), 7.66-7.69 (2H, m), 7.79-7.81 (2H, m); $^{13}$C NMR 28.3, 35.4, 55.2, 65.6, 37.8, 113.0, 113.6, 123.2, 126.9, 127.7, 129.0, 129.1, 132.0, 133.9, 139.4, 139.5, 147.3, 157.7, 158.5, 168.3; MS (FAB+) m/z 493 (M, 25), 476 (M−OH, 100)

4-(3-aminopropoxy)-4'-methoxytrityl alcohol (Step 3)

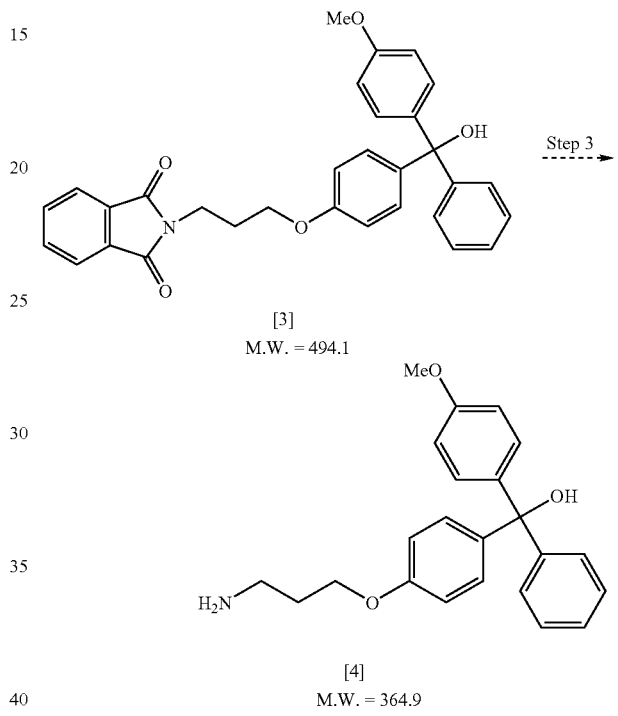

A. 17.0 g (34.4 mmoles) [3]
B. 17.3 mL (340 mmoles) Hydrazine monohydrate ME=50; Aldrich # 20794-2
C. 420 mL EtOH TLC System: Acetone/Methanol [3:2]

Using a 1L 1-neck round bottom flask equipped with a reflux condenser, (A) was dissolved in (C) and (B) was added. The mixture was heated to reflux for 1 hour. The precipitate was filtered and the solvent was evaporated. The residue was partitioned between ether and water. The ether layer was separated and the solvent evaporated in vacuo. The residue was azeotroped twice with 200 mL of methanol. TLC analysis showed a single spot. The material was moved to step 4 without further purification.

Theoretical Yield: 12.6 g

Actual Yield 14.2 g [100%]

$^1$H NMR (CDCl$_3$) 1.79-1.86 (2H, m), 2.20 (1H, br s), 2.77 (2H, t, J=7.0), 3.75 (3H, s), 3.95 (2H, t, J=6.2), 6.77-6.80 (4H, m), 7.14-7.18 (4H, m), 7.20-7.27 (5H, m); $^{13}$C NMR (CDCl$_3$) 32.6, 39.0, 55.1, 57.8, 65.7, 81.0, 112.9, 113.4, 126.8, 127.6, 127.7, 129.1, 139.7, 147.5, 157.7, 158.3; MS (ESI−) m/z 362 (M−1, 100); (ESI+) m/z 364 (M+1, 100), 727 (M$_2$+1, 37)

4-(3-(4-nitrophenoxycarboxyl)aminopropoxy)-4'-methoxy-trityl alcohol (Step 4)

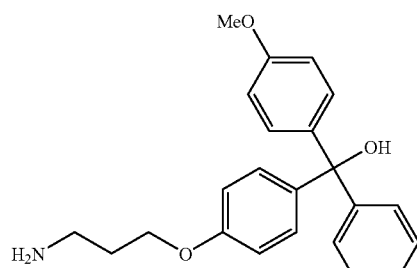

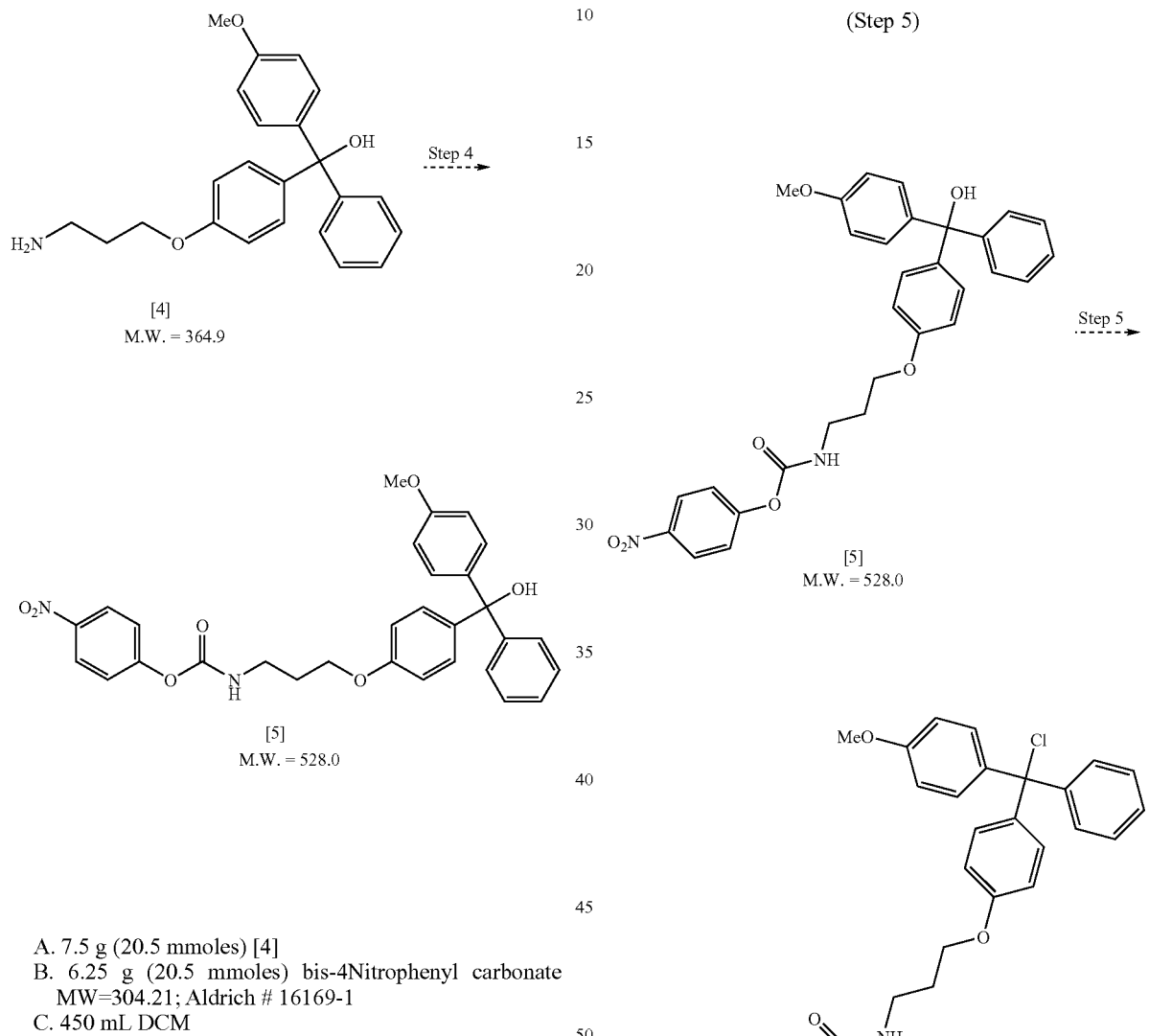

A. 7.5 g (20.5 mmoles) [4]
B. 6.25 g (20.5 mmoles) bis-4Nitrophenyl carbonate MW=304.21; Aldrich # 16169-1
C. 450 mL DCM TLC System: Acetone/Methanol [9:1]

Using a 1 L 1-neck round bottom flask, (A) was dissolved in (C) and (B) was added. The mixture was stirred for 24 hours at ambient temperature. TLC showed completion by spot to spot conversion of the starting material. Extract reaction mixture with 4×150 mL saturated $NaHCO_3$, 2×200 mL half-saturated NaCl and dried over $MgSO_4$. The product was then column purified over a silica gel column packed with HEX/EtOAc (2:1) and eluted with HEX/EtOAc (1:1) as mobile phase. The product was column purified a second time over silica gel using HEX/EtOAc/DCM (2:1:1) as mobile phase for elution of the product.

Theoretical Yield: 10.8 g

Actual Yield 7.0 g [65%]

$^1H$ NMR ($CDCl_3$) 2.02-2.08 (2H, m), 3.05 (1H, br s), 3.45-3.53 (2H, m), 3.77 (3H, s), 4.05 (2H, t, J=5.6), 5.70 (1H, t, J=5.6), 6.79-6.82 (4H, m), 7.13-7.17 (4H, m), 7.23-7.30 (7H, m), 8.18 (2H, d, J=9.1); $^{13}C$ NMR ($CDCl_3$) 28.8, 39.1, 55.1, 65.8, 81.3, 113.1, 113.6, 121.9, 125.0, 127.0, 127.7, 127.8, 129.1, 129.2, 139.3, 139.9, 144.6, 147.2, 153.1, 155.8, 157.5, 158.6; MS (FAB+) m/z 528 (M, 28), 511 (M-OH, 100)

4-(3-(4-nitrophenoxycarboxy)aminopropoxy)-4'-methoxy-trityl chloride (Step 5)

TLC System: Hexane/EtOAc [2:1]

A. 3.50 g (6.63 mmol) [5]
B. 11.6 mL (133 mmol) oxalyl chloride MW=126.9; Aldrich # 32042-0
C. 120 mL Hexane A 250 mL 3-neck round bottom flask was equipped with a cold-finger reflux/distillation condenser, magnetic stir bar, and two silicon rubber septa. (A) was suspended in (C) in the flask, and the flask was placed under argon and stirred. (B) was added to the stirring solution drop wise. Upon addition the suspended material dissolved and small bubbles formed in the flask. The reaction was refluxed overnight. The next morning the refluxing reaction consisted of a clear refluxing solution and a viscous orange-red oil on the bottom of the flask. The condenser was then set to distill and the hexanes and excess (B) removed by distillation. The remaining oil was placed under high vacuum resulting in 6.7 g of a foamed solid, used in the following reaction.

Theoretical Yield: 6.6 g

Actual Yield 6.7 g [100%]

5'-O-(4-(3-(4-nitrophenoxycarboxy)aminopropoxy)-4'-methoxytrityl)-2'-deoxythymidine Step 6

The foamed solid was then reacted with thymidine, in anhydrous pyridine, to give spot to spot conversion to the 5'-O-(4-(3-(4-Nitrophenoxycarbonyl) aminopropoxy), 4'-methoxytrityl)-2'-deoxythymidine product, shown in structure (XIIId).

5'-O-(4-(3-(4-nitrophenoxycarbonyl)-aminopropoxy)-4'-methoxytrityl)-2'-deoxythymidine $^{1}$H NMR (CDCl$_3$) 1.47 (3H, s), 2.05-2.16 (2H, m), 2.26-2.55 (2H, m), 3.35-3.53 (5H, m), 3.78 (3H, s), 4.02-4.10 (3H, m), 4.58 (1H, br s), 5.88 (1H, t, J=5.9), 6.40 (1H, t, J=7.0), 6.80-6.85 (4H, m), 7.21-7.27 (9H, m), 7.40 (2H, d, J=7.4), 7.59 (1H, s), 8.22 (2H, d, J=8.9), 9.90 (1H, s); $^{13}$C NMR (CDCl$_3$); 11.7, 28.9, 38.9, 40.8, 53.4, 55.2, 63.6, 65.8, 72.2, 84.8, 86.3, 86.8, 111.1, 113.2, 113.7, 121.9, 124.9, 127.1, 127.9, 128.0, 129.9, 130.0, 135.1, 135.9, 144.2, 144.6, 150.6, 153.2, 155.9, 157.6, 158.6, 164.1; MS (FAB+) m/z 753 (M+1, 100)

It will be apparent to one of skill in the art that the series of syntheses described above may be altered to employ analogous starting materials that react in a similar manner to give analogous products, and that such alteration of the synthesis is within ordinary skill in the art. For example, in the last step, thymidine may be replaced with N-4-dimethoxy trityl-2'-deoxycytidine to give 5'-O-(4-(3-(4-Nitrophenoxycarbonyl)-aminopropoxy)-4'-methoxytrityl)-N-4-dimethoxytrityl-2'-deoxycytidine as the final product. As another example, in step 2, the 3-bromopropyl phthalamide may be replaced with 2-bromo ethyl phthalamide to give 4-(3-phthalamidoethoxy)-4'-methoxytrityl alcohol as the product of step 2. As another example, it will be appreciated that the nucleoside moiety may be bound to the triaryl methyl linker group via either the 3'-OH or the 5'-OH. Such a modification will be accomplished by reacting a 5'-O-protected nucleoside with the trityl linker under conditions that enhance the rate of trityl reaction with secondary hydroxyls such as the addition of an acylation catalyst like N,N-dimethlyaminopyridine or silver salts as well as other techniques well know to one skilled in the art.

Furthermore, in the reaction designated as "Step 1", above, the starting materials may be modified to yield a product wherein one or more of the phenyl (or substituted phenyl) rings is replaced by an alternate aromatic ring moiety, such as substituted or unsubstituted aromatic groups such as phenyl, biphenyl, naphthanyl, indolyl, pyridinyl, pyrrolyl, thiophenyl, furanyl, annulenyl, quinolinyl, anthracenyl, and the like. Such products may then be used as alternative starting materials in the reaction designated "Step 2" (and so on through the rest of the described syntheses) to give a triaryl methyl-modified nucleotide monomer, above.

As shown in the reaction designated (XIVd), below, the 5'-linked molecules can then be reacted with a support having a reactive moiety such as amine or hydroxyl group, wherein the support is suitable for use for polynucleotide synthesis.

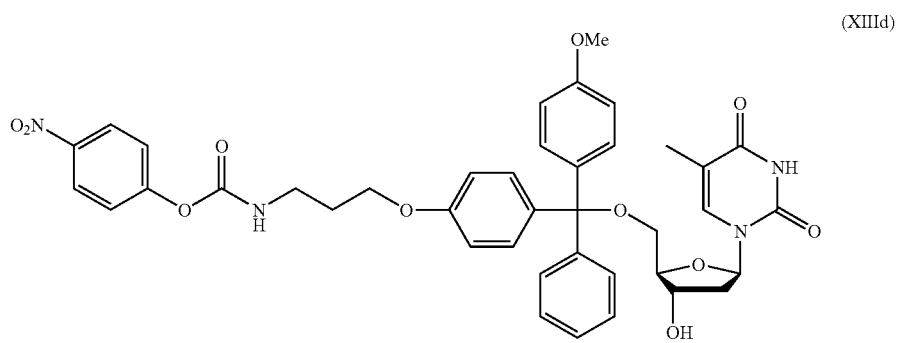

(XIIId)

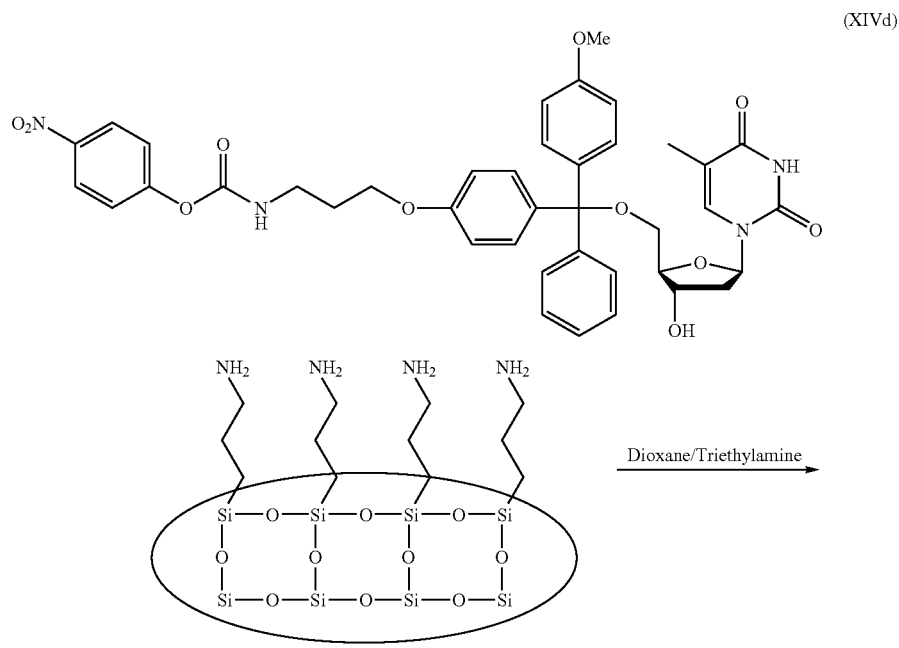

(XIVd)

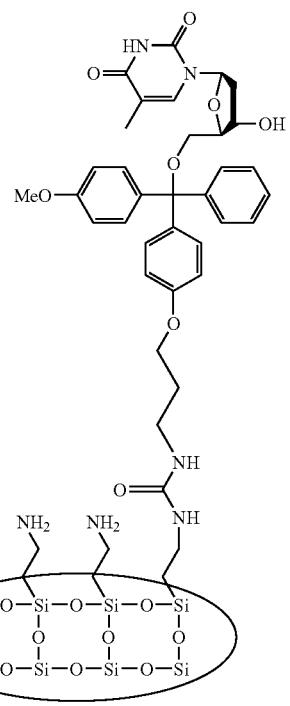

The 3'-hydroxyl of the nucleoside moiety may then be used as a starting point for performing rounds of a polynucleotide synthesis reaction to give a product in which a polynucleotide strand is bound to the substrate via the trityl group. An example of such a product is shown in the reaction designated (XVd), below, in which an oligonucleotide that is four nucleotides long has been synthesized and is bound to the substrate via the trityl moiety.

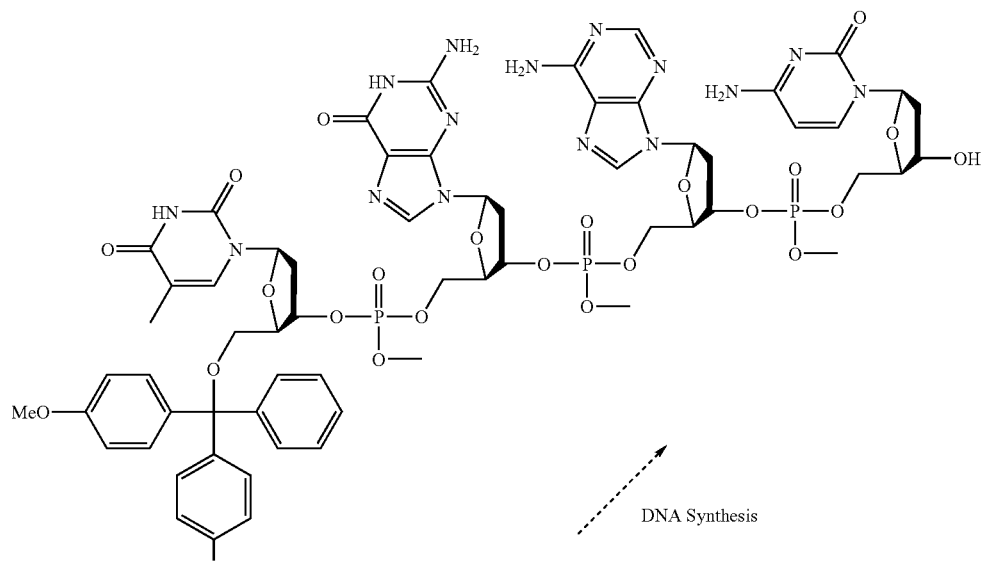

(XVd)

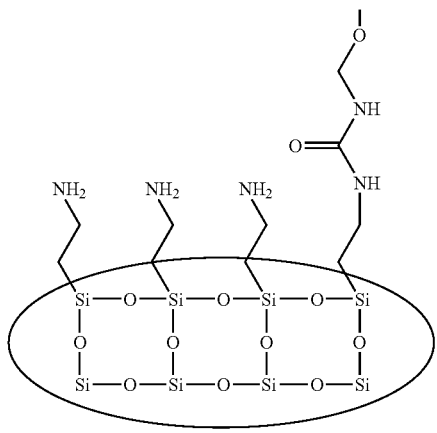

Once the synthesis is complete, the polynucleotide can be released from the support with mild acid. The products of such reaction are shown in the structures designated (XVId), below. The polynucleotide may then be, e.g. subjected to further analysis or used as desired. In certain embodiments, a strand of DNA is synthesized on the support, followed by releasing the DNA off of the support using glacial acetic acid at room temperature for 90 minutes. The resulting released DNA may then be analyzed by HPLC or capillary electrophoresis (CE).

(XVId)
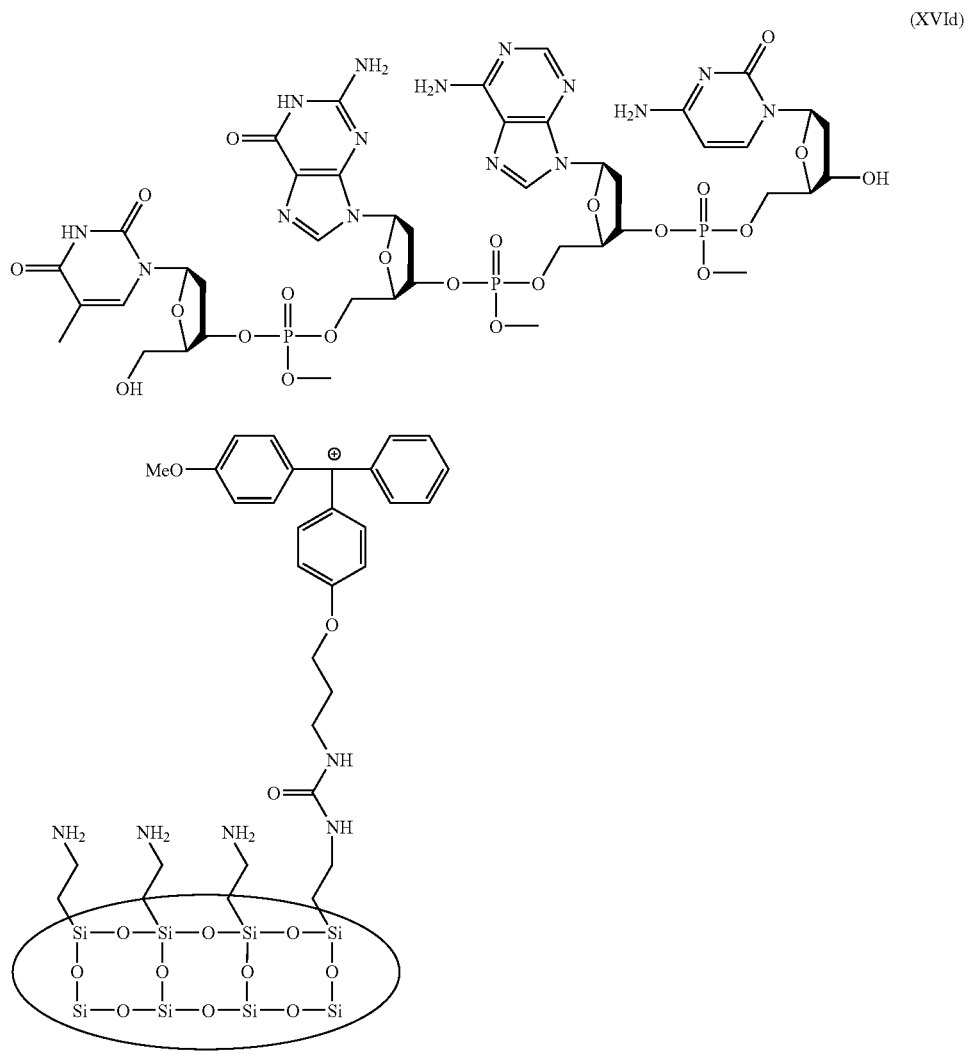
Example B
4-hydroxy-4'-methoxytrityl alcohol
Step 1
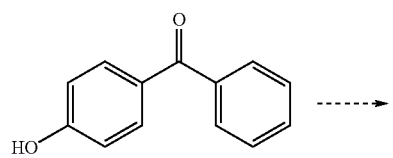
[1]
M.W. = 198.1
-continued
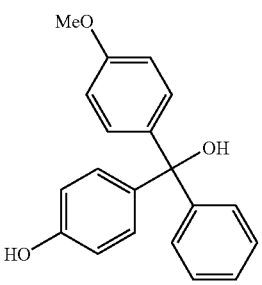
[2]
M.W. = 198.1
A. 25.0 g (126.2 mmoles) 4-hydroxy Benzophenone (1); Aldrich # H2020-2
B. 500 ml THF; Aldrich # 49446-1
C. 700 ml of a 0.5 M Solution in THF (175 mmoles) 4-Anisyl Magnesium Bromide; Alpha-Aesar # 89435

TLC System: HEX/EtOAc/Acetone (4:1:1)+0.5% Et₃N on silica gel

Using a 3-L 3-neck round bottom flask with a mechanical stirrer, U-tube thermometer and drying tube, (A) was added to (B) and the solution was cooled to 4° C. in a dry-ice/acetone bath, under Argon atmosphere. (C) was added drop wise over a period of 1 hour. Precipitate forms tan→pink color. The temperature was kept between 0-5° C. during the addition. The mixture was removed from the bath and stirred at ambient temperature (under Argon atmosphere) for 16-hours. The solvent was evaporated in vacuo. The residue was suspended in 300 ml ether and 200 mL cold water. The ether layer was extracted with 150 mL saturated NaHCO₃ and 150 mL saturated NaCl and dried with MgSO₄. The solvent was evaporated, and 66 g of an oily residue was obtained. The residue was dissolved in 50 mL DCM, 30 g silica gel added and column purified over silica gel, with DCM/AcCN (19:1) as the initial mobile phase, changing to DCM/AcCN (9:1) as mobile phase for elution of the product. The product was column purified a second time over silica gel using EtOAc/HEX (1:1) as mobile phase for elution of the product.

Theoretical Yield: 38.6 g

Actual Yield: 23.9 g [62%]

¹H NMR (CDCl₃) 3.78 (3H, s), 6.75 (2H, d, J=8.8), 6.83 (2H, d, J=8.8), 7.11 (2H, d, J=8.8), 7.17 (2H, d, J=8.8), 7.25-7.32 (5H, m); MS (ESI−) m/z 305 (M−1, 100); (ESI+) m/z 635 (M₂+Na, 33), 289 (M-H₂O, 100)

4-((3-propoxy)-tert-butyldimethylsilane)-4'-methoxytrityl alcohol

Step 2

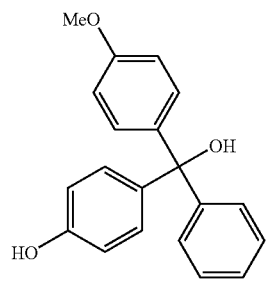

[2]
M.W. = 306.7

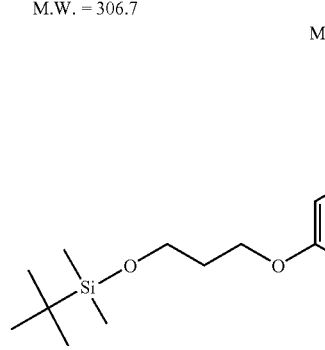

[7]
M.W. = 478.7

TLC System: DCM/AcCN [19:1]
A. 24.0 g (78.0 mmoles) [2]
B. 21.6 g (156 mmoles) potassium carbonate MW=138.1; Aldrich # 20961-9
C. 60 g (235 mmoles) (3-Bromopropoxy)-tert-butyldimethylsilane MW=253.3; Aldrich # 42,906-6
D. Single (Dry) Crystal Potassium Iodide MN 166.1; Aldrich # 22194-5
E. 600 mL Toluene Using a 2L 3-neck round bottom flask equipped with a thermometer, reflux condenser, drying tube and stir bar, (A), (B) (C), and (D) were added to (E) in sequential order. The mixture was heated to reflux for 24 hours. The solvent was evaporated. The residue was partitioned between 750 mL DCM and 300 mL water. The DCM layer was washed twice with 400 mL sat'd NaCl then dried over MgSO₄ to yield the 4-((3-Propoxy)-tert-Butyldimethylsilane)-4'-Methoxytrityl Alcohol.

Theoretical Yield: 37.3 g

Actual Yield: 16 g [43%]

MS (FAB+) m/z 479, 462 (M-OH, 100)

4-((3-propoxy)-tert-butyldimethylsilane)-4'-methoxytrityl chloride

Step 3

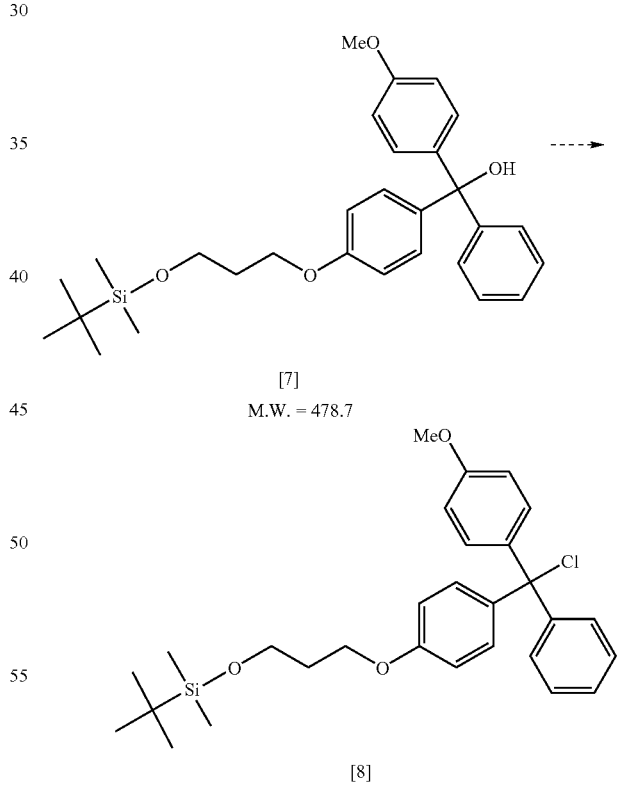

[7]
M.W. = 478.7

[8]
M.W. = 497.1

TLC System: Hexane/EtOAc [2:1]
A. 5.0 g (10.44 mmol) [7]
B. 18.2 mL (208 mmol) oxalyl chloride MW=126.9; Aldrich # 32042-0
C. 150 mL Hexane A 250 mL 3-neck round bottom flask was equipped with a cold-finger reflux/distillation condenser, magnetic stir bar, and two silicon rubber septa. (A) was suspended in (C) in the flask, and the flask was placed under argon and stirred. (B) was added to the stirring solution drop wise. Upon addition the suspended material dissolved and small bubbles formed in the flask. The reaction was refluxed overnight. The next morning the refluxing reaction consisted of a clear refluxing solution and a viscous orange-red oil on the bottom of the flask. The condenser was then set to distill and the hexanes and excess (B) removed by distillation. The remaining oil was placed under high vacuum resulting in 6.7 g of a foamed solid, used in the following reaction.

Theoretical Yield: 5.2 g

Actual Yield 5.2 g [100%]

3'-O-(4-chlorophenyl)-carbonyl-2'-deoxythymidine

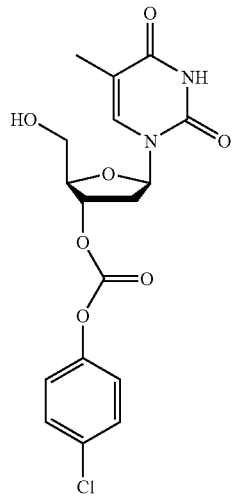

M. W. = 386.8

5'-O-(4,4'-Dimethoxytrityl)-2'-deoxythymidine (10.89 g, 20.0 mmol) was coevaporated from pyridine (3×40 mL), dissolved in pyridine (180 mL), and 4-chlorophenyl chloroformate (3.06 mL, 24.0 mmol) added with vigorous stirring. The mixture was stirred for 2 hours, solvent removed in vacuo, and the oily residue coevaporated with toluene (100 mL). The resulting oil was dissolved in dichloromethane (500 mL), extracted with saturated $NaHCO_3$ (250 mL) and brine (250 mL), dried over $MgSO_4$, and solvent evaporated to yield a viscous yellow oil. Purification by silica gel chromatography (0-2% ethanol in 100:0.1 dichloromethane:triethylamine) yielded 3'-O-(4-chlorophenyl)-carbonyl-5'-O-(4,4'-dimethoxytrityl)-2'-deoxythymidine as a white, glassy solid (10.93 g, 78.2%).

Anal. $^1$H NMR (400 MHz, $CDCl_3$) δ 9.27 (1H, s, $H_3$), 7.63 (1H, s, $H_6$), 6.85-7.42 (17H, m), 6.54 (1H, m, $H_{1'}$), 5.43 (1H, m, $H_{3'}$), 4.32 (1H, m, $H_{4'}$), 3.78 (6H, s), 3.44-3.59 (2H, m, $H_{5'}$), 2.47-2.68 (2H, m, $H_{5',5''}$), 1.40 (3H, s); $^{13}$C NMR (100.5 MHz, $CDCl_3$) δ 163.7, 158.8, 152.7, 149.7, 149.2, 144.1, 135.1, 135.0, 131.7, 130.1, 130.0, 129.8, 129.6, 128.0, 127.2, 122.2, 113.3, 111.7, 87.3, 84.3, 83.6, 79.9, 63.6, 55.2, 37.8, 11.6; MS (FAB+) m/z 698 (M, 100).

To 3'-O-(4-chlorophenyl)-carbonyl-5'-O-(4,4'-dimethoxytrityl)-2'-deoxythymidine (2.50 g, 3.58 mmol) was added a 3% solution of trichloroacetic acid in dichloromethane (400 mL) with vigorous stirring. The mixture was stirred for 3 min before pyridine/methanol (1:1) was added drop wise until the red color of the DMT cation was quenched. The mixture was extracted with saturated $NaHCO_3$ (300 mL) and brine (300 mL), dried over $MgSO_4$, and solvent removed in vacuo. Purification of the resulting oil by silica gel chromatography (0-6% ethanol in dichloromethane) afforded the 3'-O-(4-Chlorophenyl)-Carbonyl-2'-Deoxythymidine as a white powder (1.30 g, 92%);

Anal. Calcd. for $C_{17}H_{17}ClN_2O_7$: C, 51.5; H, 4.3; N, 7.1. Found: C, 51.3; H, 4.5; N, 7.0. $^1$H NMR (400 MHz, $CDCl_3$/$d_4$-MeOH) 9.57 (1H, s, $H_3$), 7.44 (1H, s, $H_6$), 7.25 (2H, d, J=8.8), 7.03 (2H, d, J=8.8), 6.17 (1H, m, $H_{1'}$), 5.27 (1H, m, $H_{3'}$), 4.17 (1H, m, $H_{4'}$), 3.83 (2H, m, $H_{5'}$), 2.42 (2H, m, $H_{2',2''}$), 1.80 (3H, s); $^{13}$C NMR (100.5 MHz, $CDCl_3$/$d_4$-MeOH) 164.1, 152.8, 150.6, 149.2, 136.7, 131.7, 129.6, 122.2, 111.4, 86.3, 84.8, 79.5, 62.4, 37.0, 12.5; MS (ESI+) m/z 397 (M+1, 100).

5'-O-4-((3-propoxy)-tert-butyldimethylsilane)-4''-methoxytrityl-3'-O-(4-chlorophenyl)-carbonyl-2'-deoxythymidine Step 4

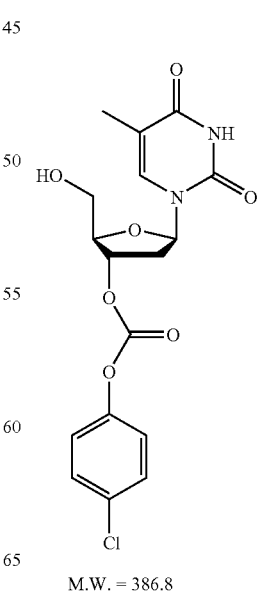

M.W. = 386.8

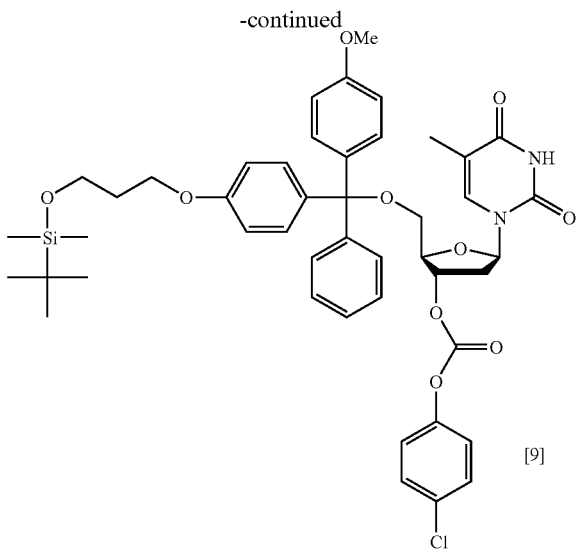

M.W. = 857.4

To 3'-O-(4-chlorophenyl)-carbonyl-2'-deoxythymidine (1.2 g, 3.1 mmol) in pyridine (35 mL) was added 4-((3-Propoxy)-tert-Butyldimethylsilane)-4'-Methoxytrityl Chloride (1.86 g, 3.75 mmol). The mixture was stirred for 4 h at which point the solvent was removed under reduced pressure. The residue was dissolved in dichloromethane, washed with 5% sodium carbonate and brine, dried (MgSO$_4$), and solvent removed in vacuo to yield a pale yellow oil. The 5'-O-4-((3-Propoxy)-tert-Butyldimethylsilane)-4"-Methoxytrityl-3'-O-(4-Chlorophenyl)-Carbonyl-2'-Deoxythymidine was isolated by silica gel chromatography using 1-4% methanoudichloromethane as eluant as a pale yellow glassy solid (2.4 g, 90.0%); MS (FAB+) m/z 743 (M, 100).

5'-O-4-(3-hydroxypropyl)-4"-methoxytrityl-3'-O-(4-chlorophenyl)-carbonyl-2'-deoxythymidine

[9] ----▶ Step 5

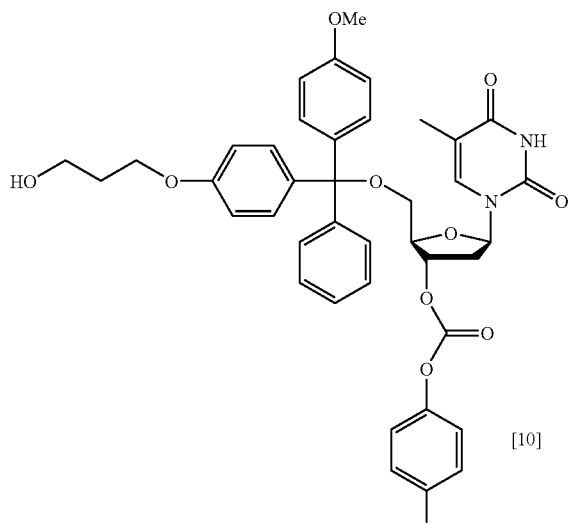

M.W. = 743.2

5'-O-4-((3-Propoxy)-tert-butyldimethylsilane)-4"-methoxytrityl-3'-O-(4-chlorophenyl)-carbonyl-2'-deoxythymidine (2.4 g, 2.8 mmol) was dissolved in anhydrous pyridine (75 mL) using a magnetic stirrer. The flask was kept anhydrous under argon and cooled in an ice/water bath. Hydrogen fluoride pyridine (100 μL) Fluka cat# 47586 was dissolved in 10 mL of anhydrous pyridine and added to the stirring flask. The reaction was allowed to stir for 30 min then evaporated to a rust brown oil. The residue was dissolved in dichloromethane, washed with 5% sodium carbonate and brine, dried (MgSO$_4$), and solvent removed in vacuo to yield a dark yellow oil. The 5'-O-4-(3-Hydroxypropyl)-4"-Methoxytrityl-3'-O-(4-Chlorophenyl)-Carbonyl-2'-Deoxythymidine was isolated by silica gel chromatography using 0-3% methanol/dichloromethane as eluant as a pale yellow glassy solid (2.4 g, 90.0%); MS (FAB+) m/z 859 (M, 100).

5'-O-4-(3-propyloxy(2-cyanoethyl N,N-diisopropylphosphoramidite))-4"-methoxytrityl-3'-O-(4-chlorophenyl)-carbonyl-2'-deoxythymidine Step 6

[10] ----▶

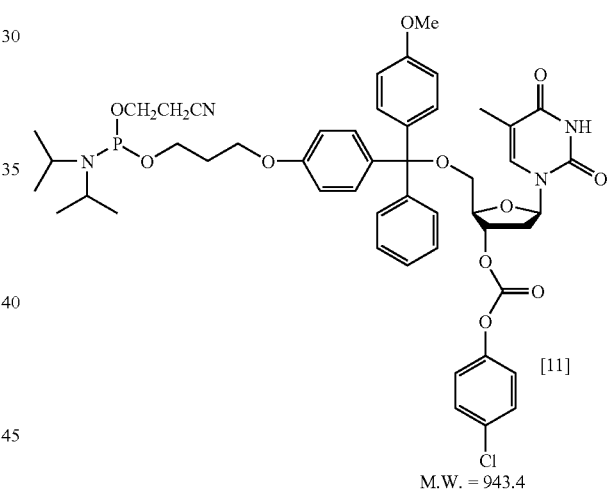

M.W. = 943.4

5'-O-4-(3-Hydroxypropyl)-4"-Methoxytrityl-3'-O-(4-Chlorophenyl)-Carbonyl-2'-Deoxythymidine 3.7 g (5.0 mmol) and tetrazole (175 mg, 2.50 mmol) were dried under vacuum for 24 h then dissolved in dichloromethane (100 mL). 2-Cyanoethyl N,N,N',N'-tetraisopropylphosphorodiamidite (2.06 mL, 6.50 mmol) was added in one portion and the mixture stirred over 1 h. The reaction mixture was washed with sat. NaHCO$_3$ (150 mL) and brine (150 mL), dried over MgSO$_4$, and applied directly to the top of a silica column equilibrated with hexanes. The dichloromethane was flashed off the column with hexanes, and the product eluted as a mixture of diastereoisomers using 1:1 hexanes:ethyl acetate then ethyl acetate. After evaporation of solvents in vacuo and coevaporation with dichloromethane, product was isolated as friable, white, glassy solids in 75% yield; $^{31}$P NMR (162.0 MHz, CDCl$_3$) 148.89, 148.85; MS (FAB+) m/z 945 (FAB-) m/z 943

It will be apparent to one of skill in the art that the series of syntheses described above may be altered to employ analogous starting materials that react in a similar manner to give analogous products, and that such alteration of the synthesis is within ordinary skill in the art. For example, thymidine may be replaced with N-4-dimethoxy trityl-2'-deoxycytidine in step 4 to give 5'-O-4-(3-propyloxy-(2-cyanoethyl N,N-diisopropyl-phosphoramidite))-4"-methoxytrityl-3'-O-(4-chlorophenyl)-carbonyl-N-4-dimethoxytrityl-2'-deoxycytidine as the final product. As another example, in step 2, the (3-bromopropoxy)-tert-butyldimethylsilane may be replaced with (4-bromobutoxy)-tert-butyldimethylsilane to give 4-((4-Butoxy)-tert-butyldimethylsilane)-4'-methoxytrityl alcohol the product of step 2. As another example, it will be appreciated that the nucleoside moiety may be bound to the triaryl methyl linker group via either the 3'-OH or the 5'-OH. Such a modification will be accomplished by reacting a 5'-O-protected nucleoside with the trityl linker under conditions that enhance the rate of trityl reaction with secondary hydroxyls such as the addition of an acylation catalyst like N,N-dimethlyaminopyridine or silver salts as well as other techniques well known to one skilled in the art.

Furthermore, in the reaction designated as "Step 1", above, the starting materials may be modified to yield a product wherein one or more of the phenyl (or substituted phenyl) rings is replaced by an alternate aromatic ring moiety, such as substituted or unsubstituted aromatic groups such as phenyl, biphenyl, naphthanyl, indolyl, pyridinyl, pyrrolyl, thiophenyl, furanyl, annulenyl, quinolinyl, anthracenyl, and the like. Such products may then be used as alternative starting materials in the reaction designated "Step 2" (and so on through the rest of the described syntheses) to give a triaryl methyl-modified nucleotide monomer, above.

As shown in the reaction designated (XVIId), below, the 5'-linked molecules can then be reacted with a support having a reactive moiety such as a hydroxyl group, thiol group, or amino group, wherein the support is suitable for use for polynucleotide synthesis.

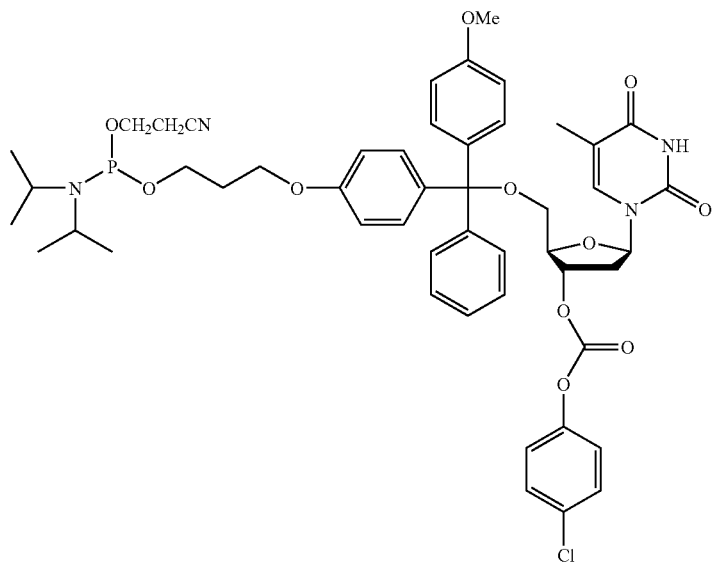

(XVIId)

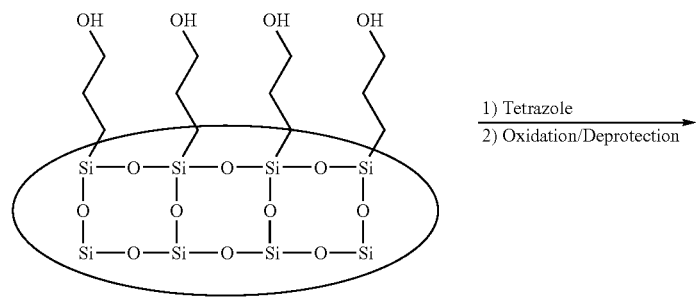

1) Tetrazole
2) Oxidation/Deprotection

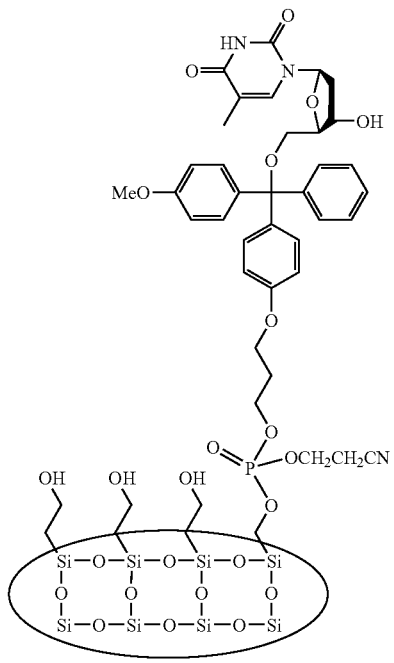

The 3'-hydroxyl of the nucleoside moiety may then be used as a starting point for performing cycles of a polynucleotide synthesis reaction to give a product in which a polynucleotide strand is bound to the substrate via the trityl group. An example of such a product is shown in the reaction designated (XVIIId), below, in which an oligonucleotide that is four nucleotides long has been synthesized and is bound to the substrate via the trityl moiety.

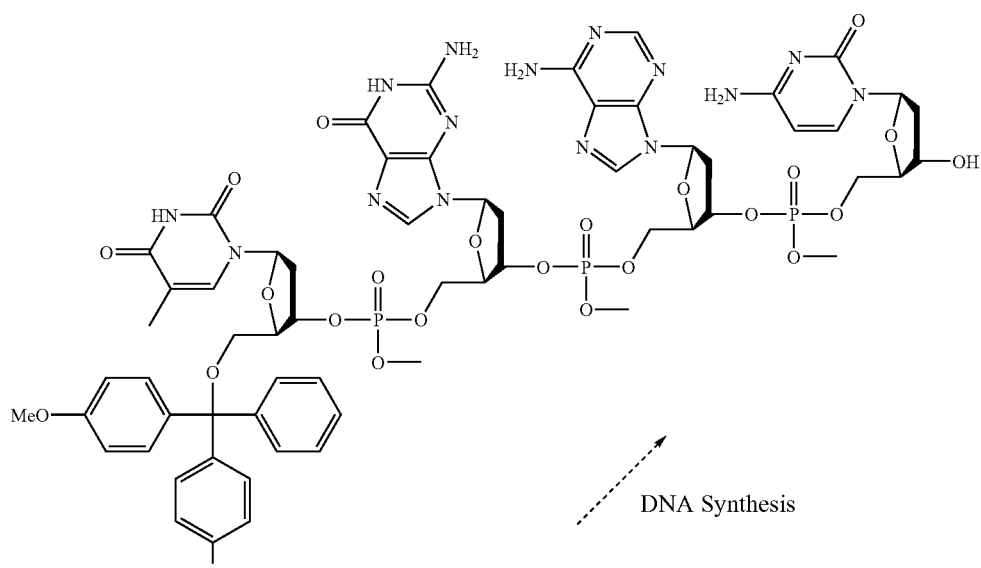

(XVIIId)

DNA Synthesis

-continued

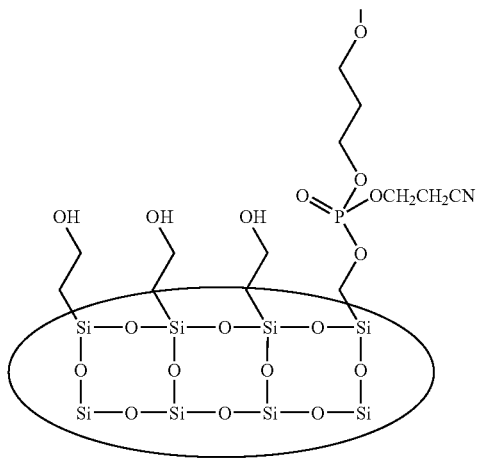

Once the synthesis is complete, the polynucleotide can be released from the support with mild acid. The products of such reaction are shown in the structures designated (XIXd), below. The polynucleotide may then be, e.g. subjected to further analysis or used as desired. In certain embodiments, a strand of DNA is synthesized on the support, followed by releasing the DNA off of the support using glacial acetic acid at room temperature for 90 minutes. The resulting released DNA may then be analyzed by HPLC or capillary electrophoresis (CE).

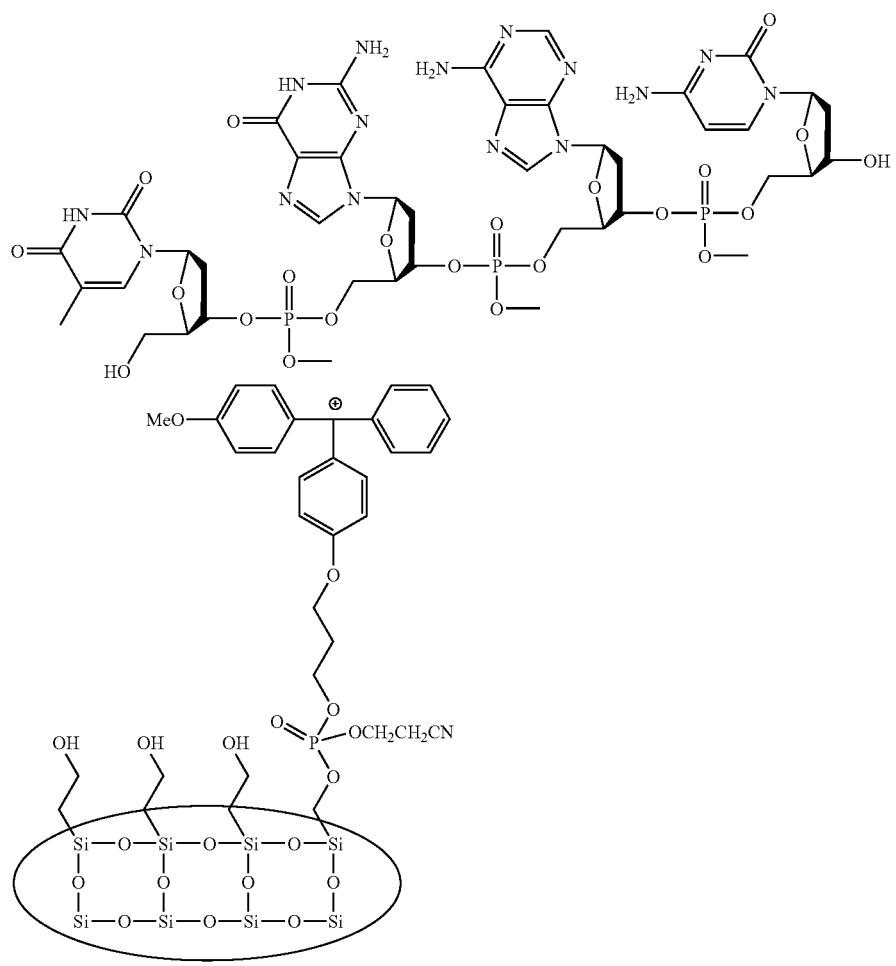

(XIXd)

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A method for synthesizing a solid-support-attached oligonucleotide or polynucleotide, the method comprising:
(a) providing a functionalized support having the structure (Id)

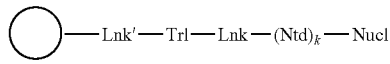

wherein the groups are defined as follows:

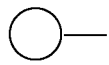

is a solid support,
Trl- is the triaryl methyl linker group having three aryl groups, wherein each of the three aryl groups are bound to a central methyl carbon, and at least one of said three aryl groups has one or more substituents, wherein one of said substituents is bound to the solid support either directly or through Lnk' and the central methyl carbon is bound to the 5'-hydroxyl of (Ntd)$_k$ either directly or through Lnk,
Lnk'- is a linking group linking the solid support and the triaryl methyl linker group, or is a bond linking the solid support and the triaryl methyl linker group,
(Ntd)$_k$- is a polynucleotide moiety having k nucleotide sub-units, wherein k is an integer in the range from zero to about 200,
Lnk- is a linking group linking the triaryl methyl linker group and the polynucleotide moiety, or is a bond linking the triaryl methyl linker group and the polynucleotide moiety, and
Nucl- is the nucleoside moiety having a reactive site hydroxyl;
(b) contacting said functionalized support with a precursor having the structure (IVd)

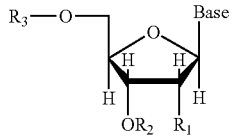

wherein the groups are defined as follows:
O and H represent oxygen and hydrogen, respectively
R$_1$ is hydrido, hydroxyl, protected hydroxyl, lower alkyl, substituted lower alkyl or alkoxy,
one of R$_2$ or R$_3$ is a hydroxyl protecting group; and the other of R$_2$ or R$_3$ is a phosphorus derivative capable of reacting with a reactive site hydroxyl of a nucleoside moiety to produce either a phosphite triester or a phosphite diester internucleotide linking moiety, and
Base is a heterocyclic base,
under conditions and for a time sufficient to result in phosphite triester internucleotide or a phosphite diester linking moiety formation;
(c) contacting the result of step (b) with a reagent comprising a nucleophilic ion or a salt thereof that exhibits an alpha effect at neutral to mildly basic pH to concurrently remove the hydroxyl protecting group from the result of step (b) and oxidize the internucleotide linking moiety wherein said reagent comprises a peroxide.

2. The method of claim 1, wherein steps (b) and (c) are repeated until an oligonucleotide or a polynucleotide having a desired sequence and length is provided.

3. The method of claim 2, further comprising wherein, after the oligonucleotide or polynucleotide having a desired sequence and length is provided, said oligonucleotide or polynucleotide is cleaved from the solid support to yield the oligonucleotide or polynucleotide free in solution, wherein the cleaving is performed by exposure of the oligonucleotide or polynucleotide attached to the solid support to mild acid.

4. The method of claim 1, wherein the triaryl methyl linker group has the structure (VId)

wherein the broken line represents a bond to Lnk, and R$_{12}$, R$_{13}$, and R$_{14}$ are independently selected from unsubstituted and substituted aryl groups, provided that one of R$_{12}$, R$_{13}$, and R$_{14}$ is substituted by being bound to the solid support via Lnk'; wherein substituted aryl is substituted with a group selected from lower alkyl, aryl, aralkyl, lower alkoxy, thioalkyl, halo, cyano, azido, sulfide, and boronyl; and lower alkyl, substituted with one or more groups selected from lower alkyl, alkoxy, thioalkyl, halo, cyano, azido, sulfide, boronyl, and fused aromatic rings.

5. The method of claim 4, wherein R$_{12}$, R$_{13}$, and R$_{14}$ are independently selected from substituted and unsubstituted phenyl groups.

6. The method of claim 4, wherein R$_{12}$, R$_{13}$, and R$_{14}$ are optionally substituted aryl groups independently selected from phenyl, biphenyl, naphthanyl, 2-thienyl, 3-thienyl, furanyl, annulenyl, and anthracenyl.

7. The method of claim 4, wherein R$_{12}$, R$_{13}$, and R$_{14}$ are independently selected from phenyl, methoxyphenyl, dimethoxyphenyl, trimethoxyphenyl, and furanyl.

8. The method of claim 4, wherein one of R$_{12}$, R$_{13}$, and R$_{14}$ is a p-methoxyphenyl, and the other two of R$_{12}$, R$_{13}$, and R$_{14}$ are phenyl, provided that one of the two phenyl is substituted by being bound to the solid support via Lnk'.

9. The method of claim 8 wherein Lnk' has the structure —O—R$_{28}$—N—C(O)N— wherein R$_{28}$ is a substituted or unsubstituted hydrocarbyl; wherein substituted hydrocarbyl is substituted with a group selected from ether, oxo-, ester-, and amido-, and/or being substituted with one or more additional groups including lower alkyl, aryl, alkoxy, thioalkyl, halo, cyano, azido, sulfide, and boronyl.

10. The method of claim 4 wherein the phosphorus derivative capable of reacting with the reactive site hydroxyl is a phosphoramidite group.

11. The method of claim 1, wherein the step (c) is conducted at neutral to mildly basic pH.

12. The method of claim 1, wherein step (c) is conducted at a pH that is greater than the $PK_a$ of said nucleophile.

13. The method of claim 12, wherein the peroxide is an inorganic peroxide of the formula $M^+OOH^-$, wherein $M^+$ is a counter ion selected from the group consisting of $H^+$, $Li^+$, $Na^+$, $K^+$, $Rb^+$ and $Cs^+$.

14. The method of claim 12, wherein the peroxide is an organic peroxide of the formula ROOH, wherein R is selected from alkyl, aryl, substituted alkyl, substituted aryl, and substituted lower alkyl, wherein
substituted aryl is substituted with a group selected from lower alkyl, aryl, aralkyl, lower alkoxy, thioalkyl, halo, cyano, azido, sulfide, and boronyl; and lower alkyl, substituted with one or more groups selected from lower alkyl, alkoxy, thioalkyl, halo, cyano, azido, carboxy, sulfide, boronyl, and fused aromatic rings;
substituted alkyl and substituted lower alkyl are substituted with a group selected from ether, oxo, ester, and amido, and/or being substituted with one or more additional groups including lower alkyl, aryl, alkoxy, thioalkyl, halo, cyano, azido, sulfide, and boronyl.

15. The method of claim 12, wherein the peroxide is selected from t-butyl hydroperoxide, m-chloroperoxybenzoic acid, and mixtures thereof.

16. The method of claim 12, wherein the peroxide has the structure of formula (Xd), (XId) or (XIId)

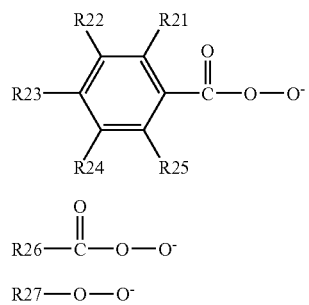

in which $R_{21}$, $R_{22}$, $R_{23}$, $R_{24}$, $R_{25}$, $R_{27}$, and $R_{36}$ are each independently selected from the group consisting of hydrido, alkyl, substituted alkyl, aryl, aralkyl, cycloalkyl, cycloalkylalkyl, substituted aralkyl, substituted cycloalkyl, and substituted cycloalkylalkyl; wherein
substituted alkyl, substituted aralkyl, substituted cycloalkyl, substituted cycloalkyalkyl are substituted with a group selected from ether, -oxo, ester, and amido, and/or being substituted with one or more additional groups including lower alkyl, aryl, alkoxy, thioalkyl, halo, cyano, azido, sulfide, and boronyl; and
substituted cycloalkynyl is substituted with a group selected from halogen, amino, carbonyl, alkoxy, carboxyl, hydrocarbyl groups, hydrocarbyl groups substituted with one or more heteroatoms. alkyl, lower alkyl, aryl, aralkyl, lower alkoxy, thioalkyl, halo, cyano, azido, sulfide, boronyl, and modified lower alkyl.

17. The method of claim 1, wherein the synthesis is conducted in the 3'-to-5' direction.

18. The method of claim 1, wherein the synthesis is conducted in the 5'-to-3' direction.

19. The method of claim 1, wherein the heterocyclic base is a naturally occurring purine or pyrimidine base.

20. A method for synthesizing an oligonucleotide or a polynucleotide, the method comprising:
(a) providing a functionalized support having the structure (Id)

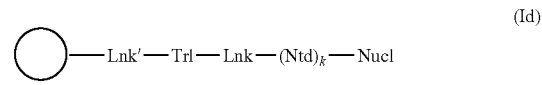

wherein the groups are defined as follows:

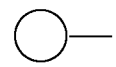

is a solid support,
Trl- is the triaryl methyl linker group having the structure (VId)

wherein the broken line represents a bond from a central methyl carbon to the 5'-hydroxyl of $(Ntd)_k$ either directly or through Lnk and $R_{12}$, $R_{13}$, and $R_{14}$ are independently selected from unsubstituted and substituted aryl groups, provided that one of $R_{12}$, $R_{13}$, and $R_{14}$ is substituted by being bound to the solid support via Lnk',
Lnk'- is a linking group linking the solid support and the triaryl methyl linker group, or is a bond linking the solid support and the triaryl methyl linker group,
$(Ntd)_k$- is a polynucleotide moiety having k nucleotide sub-units, wherein k is an integer in the range from zero to about 200,
Lnk- is a linking group linking the triaryl methyl linker group and the polynucleotide moiety, or is a bond linking the triaryl methyl linker group and the polynucleotide moiety, and Nucl- is the nucleoside moiety having a reactive site hydroxyl;
(b) contacting said functionalized support with a precursor having the structure (IVd)

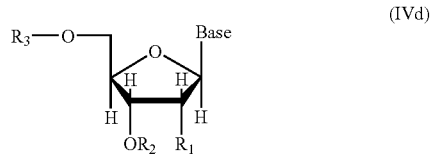

wherein the groups are defined as follows:
O and H represent oxygen and hydrogen, respectively
$R_1$ is hydrido, hydroxyl, protected hydroxyl, lower alkyl, substituted lower alkyl or alkoxy, one of $R_2$ or $R_3$ is a hydroxyl protecting group; and the other of $R_2$ or $R_3$ is a phosphorus derivative capable of reacting with a reactive site hydroxyl of a nucleoside moiety to produce either a phosphite triester or a phosphite diester intern ucleotide linking moiety, and Base is a naturally occurring purine or pyrimidine base, under conditions and for a time sufficient to result in phosphite triester or phosphite diester internucleotide linking moiety formation; and (c) contacting the result of step (b) with a peroxide reagent effective to concurrently remove the hydroxyl protecting group from the result of step (b) and oxidize the internucleotide linking moiety, and d) wherein the solid-support-attached oligonucleotide or polynucleotide is cleaved from the solid support by contacting the product of step (c) with mild acid.

* * * * *

UNITED STATES PATENT AND TRADEMARK OFFICE
CERTIFICATE OF CORRECTION

PATENT NO. : 7,585,970 B2
APPLICATION NO. : 10/652049
DATED : September 8, 2009
INVENTOR(S) : Douglas J Dellinger et al.

It is certified that error appears in the above-identified patent and that said Letters Patent is hereby corrected as shown below:

In column 54, lines 29-35, in Claim 4, delete " 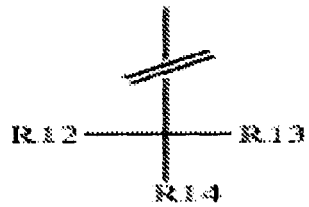 " and insert -- 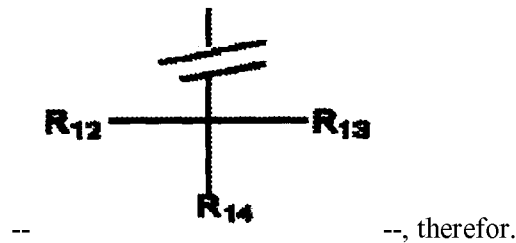 --, therefor.

In column 55, line 9, in Claim 12, delete "PK$_a$" and insert -- pKa --, therefor.

In column 55, lines 38-48, in Claim 16, delete " 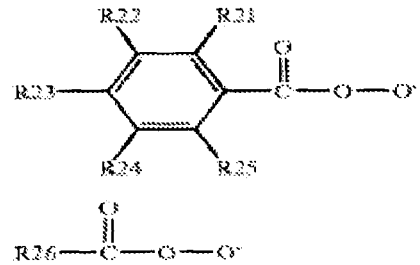 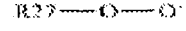 " and insert Signed and Sealed this Ninth Day of November, 2010

David J. Kappos
*Director of the United States Patent and Trademark Office*

-- 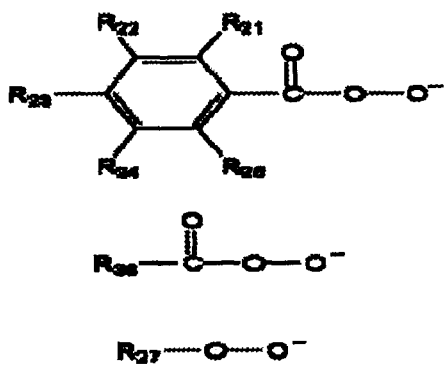 --, therefor.

In column 55, line 65, in Claim 16, delete "heteroatoms. alkyl," and insert -- heteroatoms, alkyl, --, therefor.

In column 56, lines 28-34, in Claim 20, delete " 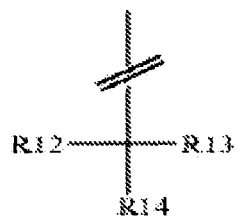 " and insert -- 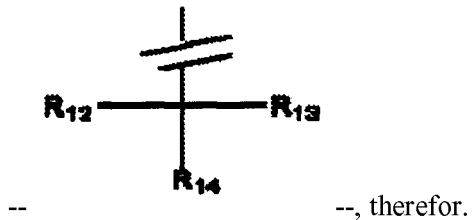 --, therefor.

In column 56, lines 48-52, in Claim 20, delete "Lnk- is a linking group linking the triaryl methyl linker group and the polynucleotide moiety, or is a bond linking the triaryl methyl linker group and the polynucleotide moiety, and Nucl- is the nucleoside moiety having a reactive site hydroxyl;" and insert -- Lnk- is a linking group linking the triaryl methyl linker group and the polynucleotide
moiety, or is a bond linking the triaryl methyl linker group and the polynucleotide moiety, and
Nucl- is the nucleoside moiety having a reactive site hydroxyl; --, therefor.

In column 57, line 5, in Claim 20, delete "intern ucleotide" and insert -- internucleotide --, therefor.